(12) United States Patent
Michejda et al.

(10) Patent No.: US 7,504,430 B2
(45) Date of Patent: Mar. 17, 2009

(54) MALEIIMIDE ANTI-TUMOR PHOSPHATASE INHIBITORS

(75) Inventors: Christopher J. Michejda, North Potomac, MD (US); Maria Michejda, legal representative, North Potomac, MA (US); Wei Yao, New Milford, NJ (US); Brian I. Carr, Glenshaw, PA (US); Siddhartha Kar, Pittsburgh, PA (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 165 days.

(21) Appl. No.: 11/508,605

(22) Filed: Aug. 22, 2006

(65) Prior Publication Data

US 2008/0039518 A1    Feb. 14, 2008

Related U.S. Application Data

(63) Continuation-in-part of application No. PCT/US2005/005742, filed on Feb. 22, 2005.

(60) Provisional application No. 60/546,841, filed on Feb. 22, 2004.

(51) Int. Cl.
    *A61K 31/4015*    (2006.01)
    *C07D 207/24*    (2006.01)
    *C07D 207/456*    (2006.01)

(52) U.S. Cl. ............... 514/425; 548/544; 548/548; 548/549

(58) Field of Classification Search ............... 514/425; 548/544, 546, 547, 565, 578, 577, 543, 548, 548/549

See application file for complete search history.

(56) References Cited

U.S. PATENT DOCUMENTS 4,172,836 A * 10/1979 Baumann et al. ............ 548/546

OTHER PUBLICATIONS

Hulubei et al., Synthesis and characterization of new functional bismaleimides, 2000, High Perform. Polym., 12, p. 248.*
Aldridge et al., A New Tricarboxylic Acid Anhydride from *Paecilomyces variotii*, 1979, J.C.S. Perkin I, p. 2134.*
Remington et al., The Science and Practice of Pharmacy, 2000, Lippincott Williams and Wilkins, 20th Edition, 218-220.*

* cited by examiner

*Primary Examiner*—Kamal A Saeed
*Assistant Examiner*—Kristin Bianchi
(74) *Attorney, Agent, or Firm*—Edwards Angell Palmer & Dodge LLP; Peter F. Corless; Christine C. O'Day

(57) ABSTRACT

The present invention features maleiimide compounds, pharmaceutical compositions of maleiimide compounds and methods of treating a patient suffering from cancer, the method comprising administering to a patient one or more maleiimide compounds of the invention.

41 Claims, 1 Drawing Sheet

MALEIIMIDE ANTI-TUMOR PHOSPHATASE INHIBITORS

CROSS-REFERENCE TO RELATED APPLICATIONS

This application claims benefit as a continuation-in-part of PCT application PCT/US05/05742, filed Feb. 22, 2005 and U.S. patent application 60/546,841, filed Feb. 22, 2004, the contents of which are incorporated by reference in their entirety.

STATEMENT REGARDING FEDERALLY SPONSORED RESEARCH OR DEVELOPMENT

Research supporting this application was carried out by the United States of America as represented by the Secretary, Department of Health and Human Services.

BACKGROUND OF THE INVENTION

1. Field of the Invention

The present invention provides maleiimide compounds and pharmaceutical compositions comprising same. The present invention further provides methods of regulating protein phosphorylation and dephosphorylation by phosphatases inhibition and methods for treating patients suffering from cancer.

2. Background

Protein phosphorylation and dephosphorylation are important in mammalian cells for intracellular control of protein function and signaling. Two general types of mammalian protein phosphatases, enzymes that remove phosphate residues from proteins, have been identified: S/T specific (protein serine/threonine, PSTP) and Y specific (protein tyrosine, PTP). There is however an important class of dual specificity (DSP) phosphatases that is unique in its ability to dephosphorylate both phospho-tyrosine and phospho-threonine/serine on the same protein substrate (Wera, S, and B. A. Hemmings, *Serine/threonine protein phosphatases. Biochem J,* 1995. 311 (Pt 1): p. 17-29). The DSPs all exhibit the conserved $HCX_5R$ motif also seen in the active site of PTPs, where H is a highly conserved histidine, C is the catalytic cysteine, the five X residues form a loop in which all the amide nitrogens hydrogen-bond to the phosphate of the substrate, and R is a highly conserved arginine that hydrogen-bonds to the phosphorylated amino acid of the substrate. DSPs display a marked preference for cyclin-dependent kinases and MAP-kinases and are recognized as an important group of regulators of cell cycle control and mitogenic signal transduction. See, for example, Keyse, S. M, *An emerging family of dual specificity MAP kinase phosphatases. Biochim Biophys Acta,* 1995. 1265(2-3): p. 152-60; Denu, J. M., et al., *Visualization of intermediate and transition-state structures in protein-tyrosine phosphatase catalysis. Proc Natl Acad Sci USA,* 1996. 93(6): p. 2493-8; Galaktionov, K., X. Chen, and D. Beach, *Cdc25 cell-cycle phosphatase as a target of c-myc. Nature,* 1996. 382(6591): p. 511-7; and Maehama, T. and J. E. Dixon, *The tumor suppressor, PTEN/MMAC1, dephosphorylates the lipid second messenger, phosphatidylinositol 3,4,5-trisphosphate. J Biol Chem,* 1998. 273(22): p. 13375-8. The Cdc25 protein phosphatases are important members of the DSPs that control cell cycle progression by activating cyclin-dependent kinases (cdk) and participate in Raf-1 mediated cell signaling (Nilsson, I. and I. Hoffmann, *Cell cycle regulation by the Cdc25 phosphatase family. Prog Cell Cycle Res,* 2000. 4: p. 107-14; and Xia, K., et al., *Tyrosine phosphorylation of the proto-oncoprotein Raf-1 is regulated by Raf-1 itself and the phosphatase Cdc25A. Mol Cell Biol,* 1999. 19(7): p. 4819-24). Three homologs of Cdc25 have been found in mammals, Cdc25A, Cdc25B and Cdc25C (Sadhu, K., et al., *Human homolog of fission yeast cdc25 mitotic inducer is predominantly expressed in G2. Proc Natl Acad Sci USA,* 1990. 87(13): p. 5139-43; Millar, J. B., et al., *p55CDC25 is a nuclear protein required for the initiation of mitosis in human cells. Proc Natl Acad Sci USA,* 1991. 88(23): p. 10500-4; and Nagata, A., et al., *An additional homolog of the fission yeast cdc25+ gene occurs in humans and is highly expressed in some cancer cells. New Biol,* 1991. 3(10): p. 959-68). Cdc25A is important for G1/S phase transition (Jinno, S., et al., *Cdc25A is a novel phosphatase functioning early in the cell cycle. Embo J,* 1994. 13(7): p. 1549-56), although it may also have some role in the initiation of mitosis (Molinari, M., et al., *Human Cdc25A inactivation in response to S phase inhibition and its role in preventing premature mitosis. EMBO Rep,* 2000. 1(1): p. 71-9). Both Cdc25B and Cdc25C are regulators of G2-M transition and S-phase progression (Lammers, R., et al., *Differential activities of protein tyrosine phosphatases in intact cells. J Biol Chem,* 1993. 268(30): p. 22456-62). Cdc25A and Cdc25B are over expressed in many cancers and are associated with poor prognosis (Galaktionov, K., X. Chen, and D. Beach, *Cdc25 cell-cycle phosphatase as a target of c-myc. Nature,* 1996. 382(6591): p. 511-7; Galaktionov, K, et al., *CDC25 phosphatases as potential human oncogenes. Science,* 1995. 269(5230): p. 1575-7; Gasparotto, D., et al., *Overexpression of CDC25A and CDC25B in head and neck cancers. Cancer Res,* 1997. 57(12): p. 2366-8; Hernandez, S., et al., *cdc25 cell cycle-activating phosphatases and c-myc expression in human non-Hodgkin's lymphomas. Cancer Res,* 1998. 58(8): p. 1762-7; and Wu, W., et al., *Overexpression of cdc25A and cdc25B is frequent in primary non-small cell lung cancer but is not associated with overexpression of c-myc. Cancer Res,* 1998. 58(18): p. 4082-5). Potent and selective inhibitors of Cdc25 would thus be attractive candidates as potential anticancer agents.

A few Cdc25 phosphatase inhibitors have been reported to date: dephostatin, sulfurcin, dnacin A1 and B1, vitamin $K_3$ and analogs and other naphthoquinone analogs, azido-homooxa steroid, alkyllysophospholipid analogs, and coscinosulfate. See, for example, Imoto, M, et al., *Dephostatin, a novel protein tyrosine phosphatase inhibitor produced by Streptomyces. I. Taxonomy, isolation, and characterization. J Antibiot (Tokyo),* 1993. 46(9): p. 1342-6; Cebula, R. E. B., J. L.; Boisclair, M. D.; Mansuri, M. M.; Pal, K.; Bockovich, N. J., *Synthesis and phosphatase inhibitory activity of analogs of sulfurcin. Bioorg. Med. Chem. Lett,* 1997. 7: p. 2015-2020; Horiguchi, T, et al., *Dnacin A1 and dnacin B1 are antitumor antibiotics that inhibit cdc25B phosphatase activity. Biochem Pharmacol,* 1994. 48(11): p. 2139-41; Borgne, A. and L. Meijer, *Sequential dephosphorylation of p34(cdc2) on Thr-14 and Tyr-15 at the prophase/metaphase transition. J Biol Chem,* 1996. 271(44): p. 27847-54; Tamura, K., et al., *Cdc25 inhibition and cell cycle arrest by a synthetic thioalkyl vitamin K analogue. Cancer Res,* 2000. 60(5): p. 1317-25; Ham, S. W., et al., *Naphthoquinone analogs as inactivators of cdc25 phosphatase. Bioorg Med Chem Lett,* 1998.8(18): p. 2507-10; Peng, H., et al., *Novel CDC25A phosphatase inhibitors from pyrolysis of 3-alpha-azido-B-homo-6-oxa-4-cholesten-7-one on silica gel. J Med Chem,* 1998. 41(24): p. 4677-80; Koufaki, M., et al., *Alkyl and alkoxyethyl antineoplastic phospholipids. J Med Chem,* 1996. 39(13): p. 2609-14; Loukaci, A. S., Isabelle Le; Samadi, Mohammad; Leclerc, Sophie; Damiens, Eve; Laurent, Meijer; Debitus, Cecile; Guyot, Michele, *Coscinosulfate, a CDC25 Phospho-* tase Inhibitor from the Sponge Coscinoderma Mathewsi. Bioorg. Med. Chem. Lett, 2001. 9: p. 3049-3054.

An attractive feature of vitamin $K_3$ and its analogs as a broad spectrum antitumor agents lie with their relatively low toxicity ($LC_{50}$ for Vitamin $K_3$ orally in mice, 0.5 g/kg) in comparison with other quinone antitumor agents. The synthetic vitamin $K_3$ analogs, are more potent growth inhibitors in human Hep3B cell line and inhibitors of DNA synthesis in normal rat hepatocytes. However, the activity was generally in the low micromolar range. We synthesized several new vitamin K analogs, which were only marginally better than the best non-toxic compound that was available Cpd 5,2-(2-mercaptoethanol)-3-methyl-1,4-naphthoquinone.

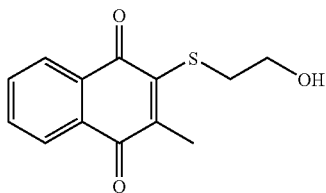

Cpd 5

Improvements in the activity of vitamin K analogs as phosphatase inhibitors is expected to come at the expense of greater general toxicity since the vitamin K compounds are quinines, which are known to be generally toxic because of redox cycling and the concomitant formation of reduced oxygen species.

Thus, it would be desirable to provide new vitamin K analogs which do not contain a naphthoquinone ring system and are thus avoid the toxicity associated with vitamin K naphthaquinone compounds due to redox cycling. Moreover, it would be desirable to provide new compounds having high affinity and selectivity for a variety of phosphatase enzymes, or more particularly DSP enzymes. It would be further desirable to provide a new class of phosphatase inhibitors which are easy to prepare in a minimal number of steps. It would also be desirable to have methods of inhibiting phosphatase and methods of treating a variety of cancers using the new non-naphthaquinone vitamin K analogs.

SUMMARY OF THE INVENTION

The present invention provides compounds according to Formula I:

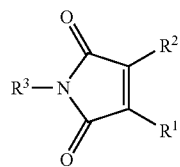

I wherein:

$R^1$ and $R^2$ are independently selected from hydrogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, or optionally substituted aminoalkyl;

$R^3$ is optionally substituted alkyl, optionally substituted alkenyl, optionally substituted alkynyl, optionally substituted carbocyclic aryl, optionally substituted heteroaryl, optionally substituted cycloalkyl, or optionally substituted heteroalicyclic group; and pharmaceutically acceptable salts thereof.

The present invention further provides pharmaceutical compositions comprising one or more compounds according to Formula I and at least one pharmaceutically acceptable carrier.

The present invention further provides methods of treating or preventing cancer comprising the administration of a compound of Formula I or any subformula thereof to a patient susceptible to or suffering from cancer. Typically, the compounds of the present invention are suitable for inhibiting tyrosine phosphatases, serine/threonine phosphatases, and/or dual specificity phosphatases (DSP). Preferred methods of the invention are suitable for use in anti-cancer therapies and comprise the administration of compounds of Formula I, alone or in combination with other anti-cancer or anti-tumor therapeutics.

Other aspects of the invention are described infra.

DETAILED DESCRIPTION OF THE INVENTION

Figure 1:
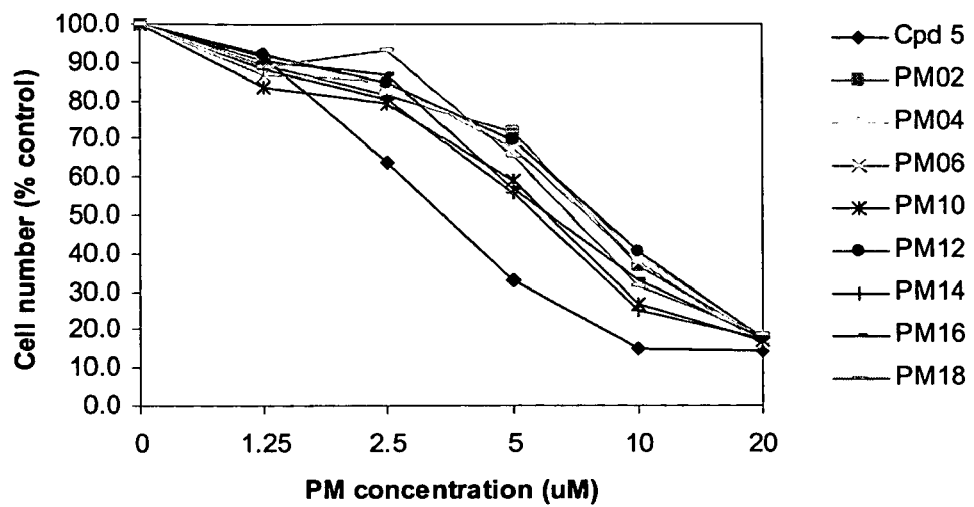
FIG. 1 is a plot of cell growth inhibition activity for 2-(2-mercaptoethanol)-3-methyl-1,4-naphthoquinone and various compounds according to Formula I.

The present invention provides a family of maleiimide compounds. Preferred maleiimide compounds include those which are capable of inhibiting dual specificity phosphatases (DSP). More particularly, the maleiimide compounds of the invention possess inhibition activity against tyrosine phosphatases, serine/threonine phosphatases, and dual specificity (DSP) phosphatases which can dephosphorylate both phospho-tyrosine and phospho-threonine/serine on the same protein substrate. More preferred are maleiimide compounds of the invention which are capable of, in vitro or in vivo, inhibiting phosphatases which are over-expressed in tumor cells of a variety of cancers.

The present invention further provides methods of inhibiting phosphatase activity by administering an effective amount of one or more maleiimide compounds of the invention to the tumor. The invention also provides methods of treating a patient suffering from cancer which comprise the administration of a therapeutically effective amount of one or more maleiimide compounds of the invention to the patient. Preferably, administration of the maleiimide compound(s) selectively inhibits one or more phosphatases which dephosphorylate phospho-tyrosine and phospho-threonine/serine on the same protein substrate and which phosphatases are over-expressed in cancer or tumor cell lines. Thus, preferred compounds of the present invention are at least twice, or more preferably at least 5, 10, 15, or 20 times more active against tumor cells as compared to untransformed cells, e.g., non-tumor cells.

Certain preferred compounds of Formula I, include those compounds in which $R^3$ is optionally substituted aryl comprising between one and three aromatic carbocyclic rings which can be fused or connected by C—C single bonds, optionally substituted heteroaryl comprising between one and three aromatic rings and between one and four heteroatoms selected from N, O, and S, or $R^3$ is optionally substituted cycloalkyl. More preferably, $R^3$ is an optionally substituted carbocyclic aryl group or an optionally substituted heteroaryl group.

In certain preferred compounds of Formula I, $R^3$ is optionally substituted phenyl, optionally substituted biphenyl, or optionally substituted 1- or 2-naphthyl. More preferably, $R^3$ is phenyl or naphthyl each of which is unsubstituted or substituted with between one and three substituents selected from the group consisting of amino, halogen, hydroxy, cyano, nitro, carboxylate, carboxamide, $C_{1-6}$alkyl, $C_{2-6}$alkenyl, $C_{2-6}$alkynyl, $C_{6-12}$aryl, $C_{3-10}$heteroaryl, $C_{1-6}$alkoxy, $C_{1-6}$mercaptoalkyl, $C_{1-6}$mercaptoalkanol, mono- or di-$C_{1-6}$alkyl amino, $C_{3-8}$cycloalkyl, $C_{2-7}$heteroalicyclic, or $C_{1-6}$aminoalkyl.

In certain other aspects of the invention, preferred compounds of Formula I include those compounds in which $R^1$ and $R^2$ are independently selected from the group consisting of $C_{1-6}$alkyl, $C_{1-6}$alkoxy, mono- and di-$C_{1-6}$alkyl amino, $C_{1-6}$mercaptoalkyl, $C_{1-6}$mercaptoalkanol, $C_{2-6}$alkenyl, and $C_{2-6}$alkynyl, each of which may be optionally substituted with one or more groups selected from halogen, hydroxy, amino, carboxylate, sulfonate, cyano, and carboxamide. More preferably, at least one of $R^1$ and $R^2$ is a $C_{1-6}$mercaptoalkanol. Still more preferred are compounds in which $R^1$ is mercaptoethanol and $R^2$ is selected from the group consisting of $C_{1-6}$alkyl, $C_{1-6}$alkoxy, mono- and di-$C_{1-6}$alkylamino, $C_{1-6}$mercaptoalkyl, $C_{1-6}$mercaptoalkanol, $C_{2-6}$alkenyl, and $C_{2-6}$alkynyl, each of which may be optionally substituted with one or more groups selected from halogen, hydroxy, amino, carboxylate, sulfonate, cyano, and carboxamide; or $R^1$ is X—$(CH_2)_n$—Y and $R^2$ is X—$(CH_2)_n$—Z, wherein X is a single bond, oxygen, sulfur or —NH—, Y is an amino residue, and Z is a carboxylate or sulfonate residue.

The invention further provides compounds of Formula I, in which $R^1$ is mercaptoethanol and $R^2$ is selected from the group consisting of $C_{1-6}$alkyl, $C_{1-6}$alkoxy, mono- and di-$C_{1-6}$ alkyl amino, $C_{1-6}$mercaptoalkyl, $C_{1-6}$mercaptoalkanol, $C_{2-6}$alkenyl, and $C_{2-6}$alkynyl, each of which may be optionally substituted with one or more groups selected from halogen, hydroxy, amino, carboxylate, sulfonate, cyano, and carboxamide; or $R^1$ is X—$(CH_2)_n$—Y and $R^2$ is X—$(CH_2)_n$—Z, wherein X is a single bond, oxygen, sulfur or —NH—, Y is an amino residue, and Z is a carboxylate or sulfonate residue; and $R^3$ is phenyl or naphthyl each of which is unsubstituted or substituted with between one and three substituents selected from the group consisting of amino, halogen, hydroxy, cyano, nitro, carboxylate, carboxamide, $C_{1-6}$alkyl, $C_{2-6}$alkenyl, $C_{2-6}$alkynyl, $C_{6-10}$-carbocyclic aryl, $C_{4-10}$heteroaryl, $C_{1-6}$alkoxy, $C_{1-6}$mercaptoalkyl, mono- or di-$C_{1-6}$alkyl amino, $C_{3-8}$cycloalkyl, $C_{2-7}$heteroalicyclic, or $C_{1-6}$aminoalkyl.

Preferred compounds according to Formula I provided by the present invention include those compounds Formula II:

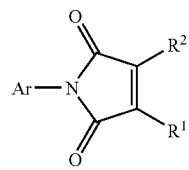

II wherein:

$R^1$ and $R^2$ are independently selected from hydrogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, or optionally substituted aminoalkyl;

Ar is optionally substituted carbocyclic aryl or optionally substituted heteroaryl; and pharmaceutically acceptable salts thereof.

In one aspect, the compounds are those of formula II, wherein:

$R^1$ is selected from hydrogen, amino, thiol, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, or optionally substituted aminoalkyl;

$R^2$ is —X—$(CH_2)$n-Y;

Ar is phenyl or naphthyl, each of which is substituted with between 0 and 5 substituents independently selected from halogen, amino, hydroxy, cyano, nitro, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, and optionally substituted aminoalkyl;

X is a single bond, O, $S(O)_p$, NH, or N($C_{1-6}$alkyl);

Y is hydroxy, carboxylate, sulfonate, carboxamide, or amino;

n is an integer of from 1 to about 8; and p is 0, 1, or 2, or a pharmaceutically acceptable salt thereof.

Particularly preferred compounds of Formula II provided by the invention include those compounds in which Ar is phenyl or naphthyl each of which is unsubstituted or substituted with between one and five residues selected from the group consisting of halogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, or optionally substituted aminoalkyl.

Yet other preferred compounds of Formula II include those compounds in which Ar is phenyl or naphthyl each of which is unsubstituted or substituted with a residue selected from the group consisting of halogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, or optionally substituted aminoalkyl.

The invention also provides compounds of Formula II, in which $R^1$ and $R^2$ are independently selected from the group consisting of alkyl, alkoxy, mono- and di-alkyl amino, mercaptoalkyl, alkenyl, and alkynyl, each of which may be optionally substituted with one or more groups selected from halogen, hydroxy, amino, carboxylate, sulfonate, cyano, and carboxamide. More preferably the invention provides compounds of Formula II in which at least one of $R^1$ and $R^2$ is a mercaptoalkanol.

Certain particularly preferred compounds of Formula II provided by the invention include those compounds in which $R^1$ is mercaptoethanol and $R^2$ is selected from the group consisting of alkyl, alkoxy, mono- and di-alkyl amino, mercaptoalkyl, alkenyl, and alkynyl, each of which may be optionally substituted with one or more groups selected from halogen, hydroxy, amino, carboxylate, sulfonate, cyano, and carboxamide; or $R^1$ is X—$(CH_2)_n$—Y and $R^2$ is X—$(CH_2)_n$—Z, wherein X is a single bond, oxygen, sulfur or —NH—, Y is an amino residue, and Z is a carboxylate or sulfonate residue.

Yet other preferred compounds of the Formula II provided by the invention include those compounds in which:

$R^1$ is mercaptoethanol and $R^2$ is selected from the group consisting of alkyl, alkoxy, mono- and di-alkyl amino, mercaptoalkyl, alkenyl, and alkynyl, each of which may be optionally substituted with one or more groups selected from halogen, hydroxy, amino, carboxylate, sulfonate, cyano, and carboxamide; or $R^1$ is X—$(CH_2)_n$—Y and $R^2$ is X—$(CH_2)_n$—Z, wherein X is a single bond, oxygen, sulfur or —NH—, Y is an amino residue, and Z is a carboxylate or sulfonate residue; and Ar is phenyl or naphthyl each of which is unsubstituted or substituted with between one and three substituents selected from the group consisting of amino, halogen, hydroxy, cyano, nitro, carboxylate, carboxamide, $C_{1-6}$alkyl, $C_{2-6}$alkenyl, $C_{2-6}$alkynyl, phenyl, tolyl, 5- or 6-member heterocycles having between 1 and 3 ring heteroatoms selected from N, O, and S, $C_{1-6}$alkoxy, $C_{1-6}$mercaptoalkyl, $C_{1-6}$mercaptoalkanol, mono- or di-$C_{1-6}$alkyl amino, $C_{3-8}$cycloalkyl, or $C_{1-6}$-aminoalkyl.

Other preferred compounds according to Formula I or Formula II include those compounds represented by Formula III:

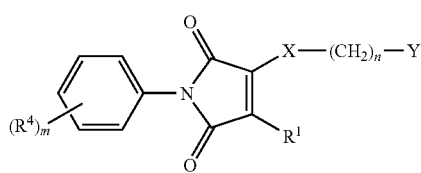

III wherein:

$R^1$ is selected from hydrogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, or optionally substituted aminoalkyl;

$R^4$ is selected from the group consisting of halogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, and optionally substituted aminoalkyl;

X is a single bond, O, S, NH, or N($C_{1-6}$alkyl)

Y is hydrogen, hydroxy, carboxylate, sulfonate, amino, m is an integer of from 0 to 5;

n is an integer of from 1 to about 8; and pharmaceutically acceptable salts thereof.

In one aspect, the compounds are those of Formula III, wherein:

$R^1$ is independently selected from hydrogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, or optionally substituted aminoalkyl;

$R^4$ is selected from the group consisting of halogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, and optionally substituted aminoalkyl;

X is a single bond, O, $S(O)_p$, NH, or N($C_{1-6}$alkyl)

Y is hydroxy, carboxylate, sulfonate, carboxamide, or amino;

m is an integer of from 0 to 5;

n is an integer of from 1 to about 8; and p is 0, 1, or 2, or a pharmaceutically acceptable salt thereof.

In another aspect, the compounds are those of any of the formulae herein, including Formula III above, wherein: $R^1$ is selected from hydrogen, amino, thiol, hydroxy, cyano, or $R^1$ is selected from $C_{1-6}$alkyl, $C_{2-6}$alkenyl, $C_{2-6}$alkynyl, $C_{1-6}$alkoxy, $C_{1-6}$mercaptoalkyl, mono- or di-($C_{1-6}$alkyl) amino, or $C_{1-6}$aminoalkyl, each of which is substituted with 0-2 substituents selected from halogen, hydroxy, amino, $C_{1-4}$alkoxy, cyano, carboxylate, or sulfonate;

$R^4$ is selected from the group consisting of halogen, amino, hydroxy, cyano, nitro, or $R^4$ is selected from $C_{1-6}$alkyl, $C_{2-6}$alkenyl, $C_{2-6}$alkynyl, phenyl, naphthyl, 5 to 7 membered heteroaryl, $C_{1-6}$alkoxy, $C_{1-6}$mercaptoalkyl, mono- or di-($C_{1-6}$alkyl)amino, and $C_{1-6}$aminoalkyl, each of which is substituted with 0-4 substituents independently selected from the group consisting of halogen, hydroxy, amino, $C_{1-6}$alkyl, $C_{1-6}$alkoxy, $C_{1-6}$haloalkyl, and $C_{1-6}$haloalkoxy;

or a pharmaceutically acceptable salt thereof.

Other aspects of the formulae herein include a compound of Formula III, wherein:

$R^1$ is —X—$(CH_2)_n$—Y, or —X—$(CH_2)_n$—Z, wherein each X is independently $S(O)_p$;

each Y is independently an amino residue, each Z is independently a carboxylate or sulfonate residue;

each n is independently 1-4; and each p is independently 0, 1, or 2, or a pharmaceutically acceptable salt thereof;

wherein n is a number from 1 to 3; and $R^4$ is selected from the group consisting of halogen, amino, hydroxy, cyano, nitro, $C_{1-6}$alkyl, $C_{2-6}$alkenyl, $C_{2-6}$alkynyl, phenyl, tolyl, $C_{1-6}$alkoxy, $C_{1-6}$mercaptoalkyl, mono- or di-$C_{1-6}$alkyl amino, $C_{3-8}$cycloalkyl, $C_{2-7}$heteroalicyclic, and $C_{1-6}$-aminoalkyl, or a pharmaceutically acceptable salt thereof;

wherein X is independently sulfur;

n is independently 2;

Y is independently hydroxyl;

$R^1$ is independently 2-hydroxyethanthiol;

$R^4$ is independently selected from the group consisting of phenyl, tolyl, $C_{1-4}$alkyl, $C_{1-4}$alkoxy, halogen, halo$C_{1-4}$alkyl, and halo$C_{1-4}$alkoxy, or a pharmaceutically acceptable salt thereof.

Certain preferred compounds of Formula III provided by the invention include those compounds wherein $R^4$ is selected from the group consisting of halogen, amino, hydroxy, cyano, nitro, carboxylate, carboxamide, $C_{1-6}$alkyl, $C_{2-6}$alkenyl, $C_{2-6}$alkynyl, phenyl, tolyl, $C_{1-6}$alkoxy, $C_{1-6}$mercaptoalkyl, mono- or di-$C_{1-6}$alkyl amino, $C_{3-8}$cycloalkyl, $C_{2-7}$heteroalicyclic, and $C_{1-6}$-aminoalkyl. More preferred compounds of Formula III, include those compounds in which X is S, and Y is OH, or the residue, X—(CH$_2$)$_n$—Y, taken in combination forms a mercaptoethanol residue (e.g., X is S, n is 2 and Y is OH).

Yet other preferred compounds of Formula III include those compounds in which $R^1$ is selected from the group consisting of $C_{1-6}$alkyl, $C_{1-6}$alkoxy, mono- and di-$C_{1-6}$alkylamino, $C_{1-6}$mercaptoalkyl, $C_{2-6}$alkenyl, and $C_{2-6}$alkynyl, each of which may be optionally substituted with one or more groups selected from halogen, hydroxy, amino, carboxylate, sulfonate, cyano, and carboxamide.

The invention further provides compounds of Formula III in which $R^4$ is halogen, amino, hydroxy, cyano, nitro, carboxylate, carboxamide, $C_{1-6}$alkyl, $C_{2-6}$alkenyl, $C_{2-6}$alkynyl, phenyl, tolyl, 5- or 6-member heterocycles having between 1 and 3 ring heteroatoms selected from N, O, and S, $C_{1-6}$alkoxy, $C_{1-6}$mercaptoalkyl, $C_{1-6}$mercaptoalkanol, mono- or di-$C_{1-6}$ alkyl amino, $C_{3-8}$cycloalkyl, or $C_{1-6}$aminoalkyl.

Additionally preferred compounds of the present invention include those compounds according to Formula IV:

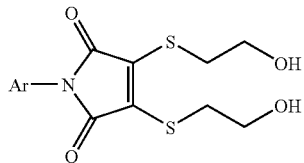

IV wherein Ar is phenyl or naphthyl each of which is unsubstituted or substituted with between one and three substituents selected from the group consisting of amino, halogen, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, or optionally substituted aminoalkyl.

Certain preferred compounds according to Formula IV include those compounds in which Ar is phenyl or naphthyl each of which is unsubstituted or substituted with between one and five residues selected from the group consisting of halogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, or optionally substituted aminoalkyl.

Other preferred compounds of Formula IV provided by the invention include those compounds in which Ar is phenyl or naphthyl each of which is unsubstituted or substituted with a residue selected from the group consisting of halogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, or optionally substituted aminoalkyl.

Yet other preferred compounds of Formula IV provided by the invention include those compounds in which Ar is phenyl or naphthyl each of which is unsubstituted or substituted with between one and three substituents selected from the group consisting of amino, halogen, hydroxy, cyano, nitro, carboxylate, carboxamide, $C_{1-6}$alkyl, $C_{2-6}$alkenyl, $C_{2-6}$alkynyl, phenyl, tolyl, 5- or 6-member heterocycles having between 1 and 3 ring heteroatoms selected from N, O, and S, $C_{1-6}$alkoxy, $C_{1-6}$mercaptoalkyl, $C_{1-6}$mercaptoalkanol, mono- or di-$C_{1-6}$ alkyl amino, $C_{3-8}$cycloalkyl, or $C_{1-6}$-aminoalkyl.

Another aspect is a compound of Formula I having the following Formula V:

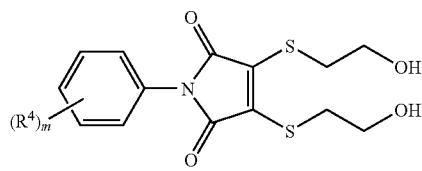

V wherein each $R^4$ is independently selected from the group consisting of halogen, amino, hydroxy, cyano, nitro, or each $R^4$ is independently selected from $C_{1-6}$alkyl, $C_{2-6}$alkenyl, $C_{2-6}$alkynyl, phenyl, naphthyl, 5 to 7 membered heteroaryl, $C_{1-6}$alkoxy, $C_{1-6}$mercaptoalkyl, mono- or di-($C_{1-6}$alkyl)amino, and $C_{1-6}$aminoalkyl, each of which is substituted with 0-4 substituents independently selected from the group consisting of halogen, hydroxy, amino, $C_{1-6}$alkyl, $C_{1-6}$alkoxy, $C_{1-6}$haloalkyl, and $C_{1-6}$haloalkoxy; and m is an integer that is 0 to 4. In another embodiment, the compound has the above formulae wherein m is a number from 1 to 3; and $R^4$ is selected from the group consisting of halogen, amino, hydroxy, cyano, nitro, $C_{1-6}$alkyl, $C_{2-6}$alkenyl, $C_{2-6}$alkynyl, phenyl, tolyl, $C_{1-6}$alkoxy, $C_{1-6}$mercaptoalkyl, mono- or di-$C_{1-6}$alkyl amino, $C_{3-8}$cycloalkyl, $C_{2-7}$heteroalicyclic, and $C_{1-6}$-aminoalkyl.

Another aspect is a compound of Formula I having the following Formula VI:

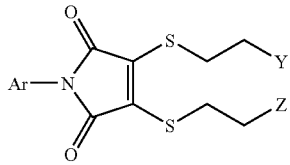

wherein Ar is phenyl or naphthyl each of which is unsubstituted or substituted with between one and three substituents selected from the group consisting of amino, halogen, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, or optionally substituted aminoalkyl;

Y is amino or mono- or di-($C_{1-4}$alkyl)amino; and

Z is a carboxylate or sulfonate residue, or a pharmaceutically acceptable salt thereof.

Another aspect is a compound of Formula I having the following Formula VII:

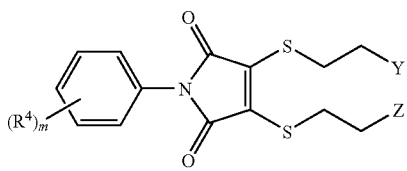

wherein each $R^4$ is independently selected from the group consisting of halogen, amino, hydroxy, cyano, nitro, or each $R^4$ is independently selected from $C_{1-6}$alkyl, $C_{2-6}$alkenyl, $C_{2-6}$alkynyl, phenyl, naphthyl, 5 to 7 membered heteroaryl, $C_{1-6}$alkoxy, $C_{1-6}$mercaptoalkyl, mono- or di-($C_{1-6}$alkyl)amino, and $C_{1-6}$aminoalkyl, each of which is substituted with 0-4 substituents independently selected from the group consisting of halogen, hydroxy, amino, $C_{1-6}$alkyl, $C_{1-6}$alkoxy, $C_{1-6}$haloalkyl, and $C_{1-6}$haloalkoxy;

m is an integer that is 0 to 4;

Y is amino or mono- or di-($C_{1-4}$alkyl)amino; and

Z is a carboxylate or sulfonate residue, or a pharmaceutically acceptable salt thereof.

Another aspect is a compound of any of the formulae herein, (e.g., formulae I-VII), wherein m is a number from 1 to 3; and $R^4$ is selected from the group consisting of halogen, amino, hydroxy, cyano, nitro, $C_{1-6}$alkyl, $C_{2-6}$alkenyl, $C_{2-6}$alkynyl, phenyl, tolyl, $C_{1-6}$alkoxy, $C_{1-6}$mercaptoalkyl, mono- or di-$C_{1-6}$alkyl amino, $C_{3-8}$cycloalkyl, $C_{2-7}$heteroalicyclic, and $C_{1-6}$aminoalkyl.

In another embodiment, the compound of any of the formulae herein is that wherein $R^4$ is not a para-carboxy substituent; that wherein $R^3$ is not a para-carboxyphenyl group; or that wherein the compound is not 3,4-Bis-(2-hydroxyethylsulfanyl)-1-(4-carboxyphenyl)-pyrrole-2,5-dione.

Other particularly preferred compounds provided by the invention include, but are not limited to,

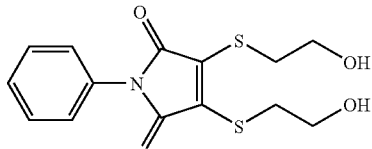

3,4-Bis-(2-hydroxy-ethylsulfanyl)-1-phenyl-pyrrole-2,5-dione;

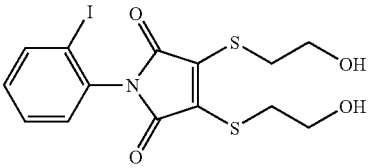

3,4-Bis-(2-hydroxy-ethylsulfanyl)-1-(2-iodophenyl)-pyrrole-2,5-dione;

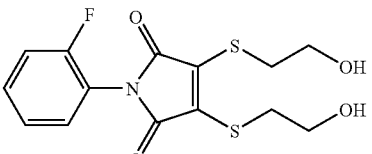

3,4-Bis-(2-hydroxy-ethylsulfanyl)-1-(2-fluorophenyl)-pyrrole-2,5-dione;

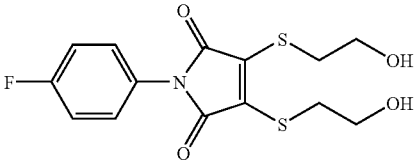

3,4-Bis-(2-hydroxy-ethylsulfanyl)-1-(4-fluorophenyl)-pyrrole-2,5-dione;

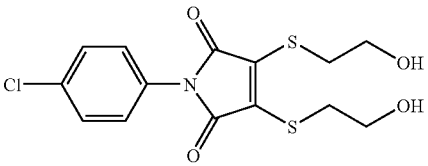

3,4-Bis-(2-hydroxy-ethylsulfanyl)-1-(4-chlorophenyl)-pyrrole-2,5-dione;

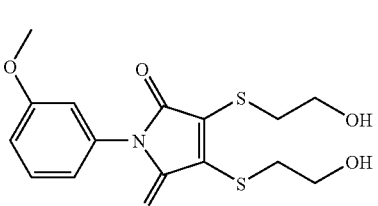

3,4-Bis-(2-hydroxy-ethylsulfanyl)-1-(3-methoxyphenyl)-pyrrole-2,5-dione;

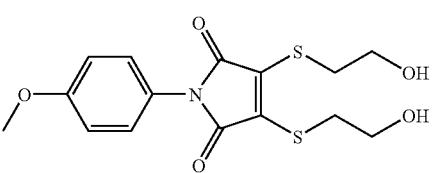

3,4-Bis-(2-hydroxy-ethylsulfanyl)-1-(4-methoxyphenyl)-pyrrole-2,5-dione;

-continued

PM-16

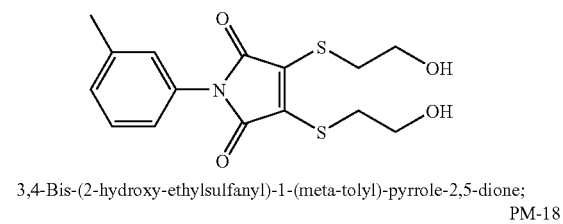

3,4-Bis-(2-hydroxy-ethylsulfanyl)-1-(meta-tolyl)-pyrrole-2,5-dione;

PM-18

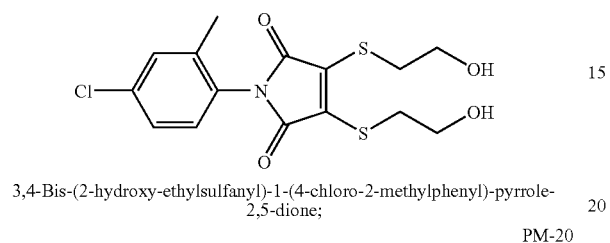

3,4-Bis-(2-hydroxy-ethylsulfanyl)-1-(4-chloro-2-methylphenyl)-pyrrole-2,5-dione;

PM-20

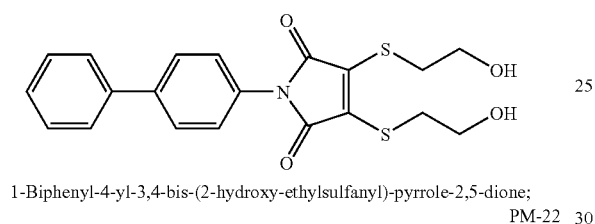

1-Biphenyl-4-yl-3,4-bis-(2-hydroxy-ethylsulfanyl)-pyrrole-2,5-dione;

PM-22

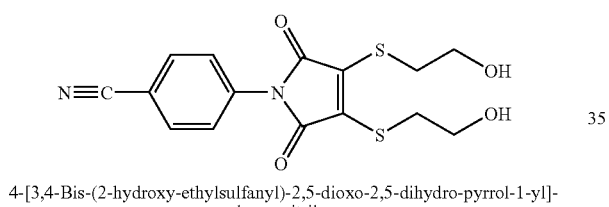

4-[3,4-Bis-(2-hydroxy-ethylsulfanyl)-2,5-dioxo-2,5-dihydro-pyrrol-1-yl]-benzonitrile;

PM-24

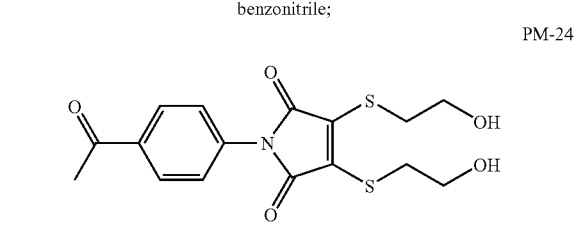

1-(4-Acetyl-phenyl)-3,4-bis-(2-hydroxy-ethylsulfanyl)-pyrrole-2,5-dione;

PM-26

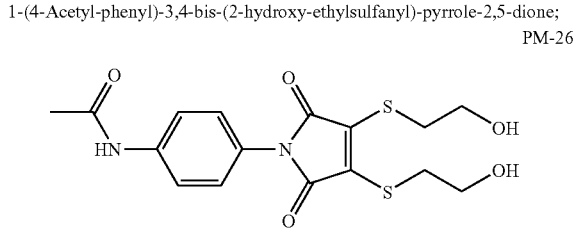

N-{4-[3,4-Bis-(2-hydroxy-ethylsulfanyl)-2,5-dioxo-2,5-dihydro-pyrrol-1-yl]-phenyl}-acetamide;

PM-28

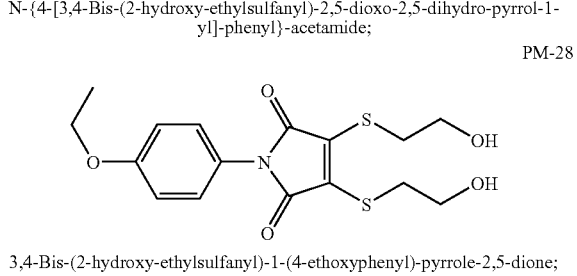

3,4-Bis-(2-hydroxy-ethylsulfanyl)-1-(4-ethoxyphenyl)-pyrrole-2,5-dione;

-continued

PM-30

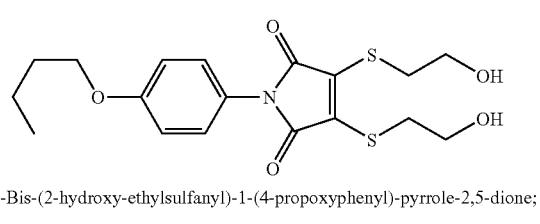

3,4-Bis-(2-hydroxy-ethylsulfanyl)-1-(4-propoxyphenyl)-pyrrole-2,5-dione;

PM-32

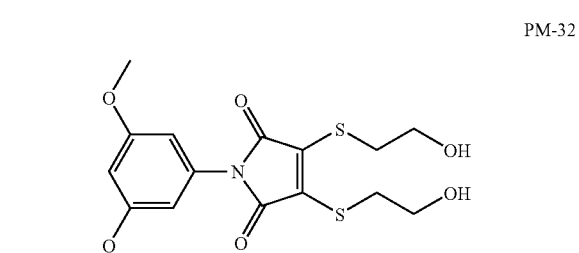

3,4-Bis-(2-hydroxy-ethylsulfanyl)-1-(3,5-dimethoxyphenyl)-pyrrole-2,5-dione;

PM-34

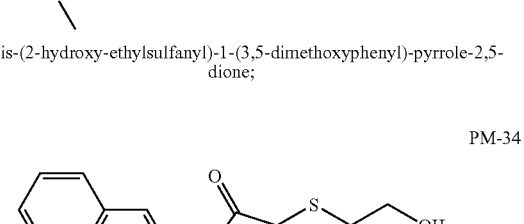

3,4-Bis-(2-hydroxy-ethylsulfanyl)-1-naphthalen-2-yl-pyrrole-2,5-dione;

PM-36

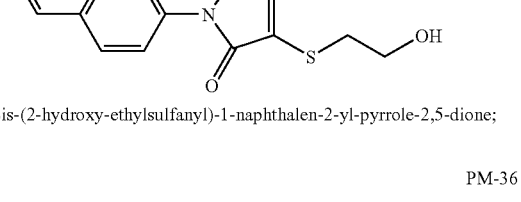

3,4-Bis-(2-hydroxy-ethylsulfanyl)-1-(trifluoromethoxyphenyl)-pyrrole-2,5-dione;

PM-38

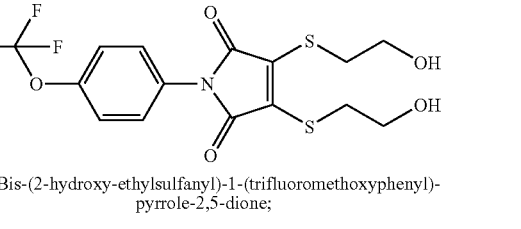

1-(4-Benzyloxy-phenyl)-3,4-bis-(2-hydroxy-ethylsulfanyl)-pyrrole-2,5-dione; and

PM-40

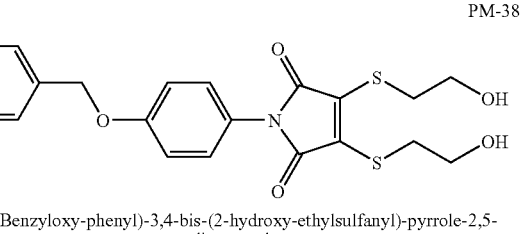

1-(4-Dimethylamino-phenyl)-3,4-bis-(2-hydroxy-ethylsulfanyl)-pyrrole-2,5-dione.

-continued

PM-42

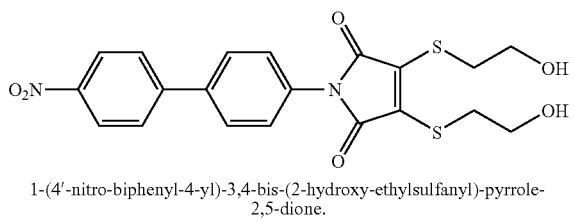

1-(4'-nitro-biphenyl-4-yl)-3,4-bis-(2-hydroxy-ethylsulfanyl)-pyrrole-2,5-dione.

Applicants have surprisingly discovered that maleiimide compounds of the present invention including those compounds represented by any one of Formula I-VII are capable of inhibiting one or more DSP phosphatases. More preferred are compounds of the invention that are capable of selectively inhibiting at least one Cdc25 phosphatase selected from the group consisting of Cdc25A, Cdc25B and Cdc25C wherein compounds capable of selectively inhibiting activity of stabilizing Cdc25A or Cdc25B are particularly preferred.

Preferred pharmaceutical compositions of the present invention comprise a pharmaceutically acceptable carrier and at least one compound according to Formula I-VII. More preferred pharmaceutical compositions comprise at least one of 3,4-Bis-(2-hydroxy-ethylsulfanyl)-1-phenyl-pyrrole-2,5-dione;

3,4-Bis-(2-hydroxy-ethylsulfanyl)-1-(2-iodophenyl)-pyrrole-2,5-dione;

3,4-Bis-(2-hydroxy-ethylsulfanyl)-1-(2-fluorophenyl)-pyrrole-2,5-dione;

3,4-Bis-(2-hydroxy-ethylsulfanyl)-1-(4-fluorophenyl)-pyrrole-2,5-dione;

3,4-Bis-(2-hydroxy-ethylsulfanyl)-1-(4-chlorophenyl)-pyrrole-2,5-dione;

3,4-Bis-(2-hydroxy-ethylsulfanyl)-1-(3-methoxyphenyl)-pyrrole-2,5-dione;

3,4-Bis-(2-hydroxy-ethylsulfanyl)-1-(4-methoxyphenyl)-pyrrole-2,5-dione;

3,4-Bis-(2-hydroxy-ethylsulfanyl)-1-(meta-tolyl)-pyrrole-2,5-dione;

3,4-Bis-(2-hydroxy-ethylsulfanyl)-1-(4-chloro-2-methylphenyl)-pyrrole-2,5-dione;

1-Biphenyl-4-yl-3,4-bis-(2-hydroxy-ethylsulfanyl)-pyrrole-2,5-dione;

4-[3,4-Bis-(2-hydroxy-ethylsulfanyl)-2,5-dioxo-2,5-dihydro-pyrrol-1-yl]-benzonitrile;

1-(4-Acetyl-phenyl)-3,4-bis-(2-hydroxy-ethylsulfanyl)-pyrrole-2,5-dione;

N-{4-[3,4-Bis-(2-hydroxy-ethylsulfanyl)-2,5-dioxo-2,5-dihydro-pyrrol-1-yl]-phenyl}-acetamide;

3,4-Bis-(2-hydroxy-ethylsulfanyl)-1-(4-ethoxyphenyl)-pyrrole-2,5-dione;

3,4-Bis-(2-hydroxy-ethylsulfanyl)-1-(4-propoxyphenyl)-pyrrole-2,5-dione;

3,4-Bis-(2-hydroxy-ethylsulfanyl)-1-(3,5-dimethoxyphenyl)-pyrrole-2,5-dione;

3,4-Bis-(2-hydroxy-ethylsulfanyl)-1-naphthalen-2-yl-pyrrole-2,5-dione;

3,4-Bis-(2-hydroxy-ethylsulfanyl)-1-(trifluoromethoxyphenyl)-pyrrole-2,5-dione;

1-(4-Benzyloxy-phenyl)-3,4-bis-(2-hydroxy-ethylsulfanyl)-pyrrole-2,5-dione;

1-(4-Dimethylamino-phenyl)-3,4-bis-(2-hydroxy-ethylsulfanyl)-pyrrole-2,5-dione;

1-(4'-nitro-biphenyl-4-yl)-3,4-bis-(2-hydroxy-ethylsulfanyl)-pyrrole-2,5-dione;

and a pharmaceutically acceptable carrier.

The recitation of a listing of chemical groups in any definition of a variable herein includes definitions of that variable as any single group or combination of listed groups. Any alternative or "preferred" listing includes embodiments that include that listing in combination with any other definitions or listing herein. Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., formulation into therapeutic products, intermediates for use in production of therapeutic compounds, isolatable or storable intermediate compounds).

The present invention further provides methods of treating or preventing cancer comprising administrating a maleiimide compound of the present invention such as the maleiimide compounds according to any one of Formula I-VII or a pharmaceutical composition comprising one or more maleiimide compounds to a patient suffering from or susceptible to cancer (e.g., a solid tumor, a disseminated tumor, liver cancer, head cancer, neck cancer, non-small cell lung cancer (NSLC), breast cancer, skin cancer, stomach cancer, tongue cancer, colon cancer). Preferred cancer patients who are suitable for the methods of the present invention include those patients suffering from one or more cancers which have a propensity to over-express at least one of DSP phosphatase including those which catalyze the dephosphorylation of protein tyrosine residues or protein threonine/serine residues. In other embodiments, the compounds herein are useful in treating or preventing cancers related to the following cell lines, or having common or analogous targets or mechanisms of activity: MCF7 and SKBR3, mammary carcinoma; FemX, melanoma; HR, gastric carcinoma; PCI, squamous cell carcinoma from tongue; LS180, colon carcinoma; and Hep3B, hepatocellular carcinoma.

Preferred methods of DSP phosphatase inhibition are performed in vitro or in vivo. More preferred methods of DSP phosphatase inhibition are performed in vivo and include treatment or prevention of cancer or other tumor disorders in mammalian patients including livestock, companion animals (dogs, cats, horses and the like), primates and humans.

Preferred methods of the invention include methods of identifying and/or selecting a subject (e.g. mammal, particularly human) that is suffering from a cancer or a growth of tumor cells which preferably over-express at least one tyrosine phosphatase, serine/threonine phosphatase, or DSP phosphatase, and more preferably over-express at least one phosphatase selected from Cdc25 (including Cdc25A, Cdc25B, and Cdc25C) and phosphatases involved in EGFR or ERK1/2 phosphorylation.

Particularly preferred methods of treating or preventing cancer and methods of inhibiting phosphatase activity include the administration of a compound selected from Formula I-VII, or a mixture thereof, or a pharmaceutical composition thereof.

Treatment methods of the invention include in general administration to a patient a therapeutically effective amount of one or more compounds of the invention. Suitable patients include those subjects suffering from or susceptible to (i.e. prophylactic treatment) a disorder or disease identified herein. Typical patients for treatment in accordance with the invention include mammals, particularly primates, especially humans. Other suitable subjects include domesticated companion animals such as a dog, cat, horse, and the like, or a livestock animal such as cattle, pig, sheep and the like.

Preferred methods of the invention include identifying and/or selecting a subject (e.g. mammal, particularly human) that is susceptible to or suffering from a condition disclosed herein, particularly a subject that is susceptible to or suffering from one or more cancers; and include those wherein the subject is actually treated (e.g., by any objective or subjective measure, a response is observed or measured) subsequent to administration of the compound or composition herein.

Also included herein are methods of reducing susceptible cancer cells, including in a subject, comprising administering to susceptible cancer cells an effective amount of any one or more of the compounds or compositions herein; and a method of inhibiting a dual specificity phosphatase activity in a subject comprising administering to the subject an effective amount of one or more of the compounds or compositions herein.

A pharmaceutical composition of the invention also may be packaged together with instructions (i.e. written, such as a written sheet) for treatment of a cancer as disclosed herein, e.g. instruction for treatment of a subject that is susceptible to or suffering from cancer, even more preferably a subject that is susceptible to or suffering from carcinomas which preferably over-express at least one tyrosine phosphatase, serine/threonine phosphatase, or DSP phosphatase, and more preferably over-express at least one phosphatase selected from Cdc25 (including Cdc25A, Cdc25B, and Cdc25C) and phosphatases involved in EGFR or ERK1/2 phosphorylation.

Compounds of the invention are suitably administered to a subject in a water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc. Also, where an acidic group is present on an inhibitor compound, a pharmaceutically acceptable salt of an organic or inorganic base can be employed such as an ammonium salt, or salt of an organic amine, or a salt of an alkali metal or alkaline earth metal such as a potassium, calcium or sodium salt. Specifically suitable pharmaceutically acceptable salts include those formed with a non-toxic cation, preferably an alkali metal cation such as K or Na, an alkaline earth metal cation such as Mg or Ca, another non-toxic metal cation such as Al or Zn or a non-toxic metalloid cation such as $NH_4^+$, piperazinium or 2-hydroxyethylammonium. Certain preferred compounds suitable for use in the methods of the invention are sufficiently water soluble in neutral for such that the y may be delivered without pre-generation of a pharmaceutically acceptable salt.

Compounds suitable for use in the methods of the present invention include any and all different single pure isomers and mixtures of two or more isomers. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with a enantiomerically enriched compound, a racemate, or a mixture of diastereomers. Preferred enantiomerically enriched compounds have an enantiomeric excess of 50% or more, more preferably the compound has an enantiomeric excess of 60%, 70%, 80%, 90%, 95%, 98%, or 99% or more. In certain preferred embodiments, achiral maleiimide compounds of the invention or only a single enantiomer or diastereomer of a chiral maleiimide compound is administered to a patient.

In the methods of the invention, compounds of the invention according to any one of Formula I-VII and pharmaceutical compositions thereof may be administered to a subject by a variety of routes including parenteral (including intravenous, subcutaneous, intramuscular and intradermal), topical (including buccal, sublingual), oral, nasal and the like.

Compounds of the invention according to any one of Formula I-VII for use in the methods of the invention can be employed, either alone or in combination with one or more other therapeutic agents, as a pharmaceutical composition in mixture with conventional excipient, i.e., pharmaceutically acceptable organic or inorganic carrier substances suitable for a desired route of administration which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc. Tablets, capsules and syrups or other fluids are generally preferred for oral administration.

A single or combination of more than one compounds of the invention according to any one of Formula I-VII may be administered in a particular therapy. In this regard, a particular therapy can be optimized by selection of an optimal maleiimide compound, or optimal "cocktail" of therapeutic agents comprising a mixture of one or more maleiimide compounds according to any one of Formula I-VII and optionally one or more additional therapeutic agents suitable for use in the treatment of cancer including other chemotherapy agents or radiotherapy agents.

It should be understood that in addition to the ingredients particularly mentioned above the formulations of this invention may include other agents conventional in the art having regard to the type of formulation in question, for example, those suitable for oral administration may include flavoring agents.

As used herein, "alkyl" is intended to include branched, straight-chain and cyclic saturated aliphatic hydrocarbon groups including alkylene, having the specified number of carbon atoms. Examples of alkyl include, but are not limited to, methyl, ethyl, n-propyl, i-propyl, n-butyl, s-butyl, t-butyl, n-pentyl, and s-pentyl. Alkyl groups typically have 1 to about 16 carbon atoms, more typically 1 to about 20 or 1 to about 12 carbon atoms. Preferred alkyl groups are $C_1$-$C_{20}$ alkyl groups, more preferred are $C_{1-12}$-alkyl and $C_{1-6}$-alkyl groups. Especially preferred alkyl groups are methyl, ethyl, and propyl.

As used herein, "heteroalkyl" is intended to include branched, straight-chain and cyclic saturated aliphatic hydrocarbon groups including alkylene, having the specified number of carbon atoms and at least one heteroatom, e.g., N, O or S. Heteroalkyl groups will typically have between about 1 and about 20 carbon atoms and about 1 to about 8 heteroatoms, preferably about 1 to about 12 carbon atoms and about 1 to about 4 heteroatoms. Preferred heteroalkyl groups include the following groups. Preferred alkylthio groups include those groups having one or more thioether linkages and from 1 to about 12 carbon atoms, more preferably from 1 to about 8 carbon atoms, and still more preferably from 1 to about 6 carbon atoms. Alylthio groups having 1, 2, 3, or 4 carbon atoms are particularly preferred. Preferred alkylsulfinyl groups include those groups having one or more sulfoxide (SO) groups and from 1 to about 12 carbon atoms, more preferably from 1 to about 8 carbon atoms, and still more preferably from 1 to about 6 carbon atoms. Alkylsulfinyl groups having 1, 2, 3, or 4 carbon atoms are particularly preferred. Preferred alkylsulfonyl groups include those groups having one or more sulfonyl ($SO_2$) groups and from 1 to about 12 carbon atoms, more preferably from 1 to about 8 carbon atoms, and still more preferably from 1 to about 6 carbon atoms. Alylsulfonyl groups having 1, 2, 3, or 4 carbon atoms are particularly preferred. Preferred aminoalkyl groups include those groups having one or more primary, secondary and/or tertiary amine groups, and from 1 to about 12 carbon atoms, more preferably from 1 to about 8 carbon atoms, and still more preferably from 1 to about 6 carbon atoms. Aminoalkyl groups having 1, 2, 3, or 4 carbon atoms are particularly preferred.

As used herein, "heteroalkenyl" is intended to include branched, straight-chain and cyclic saturated aliphatic hydrocarbon groups including alkenylene, having the specified number of carbon atoms and at least one heteroatom, e.g., N, O or S. Heteroalkenyl groups will typically have between about 1 and about 20 carbon atoms and about 1 to about 8 heteroatoms, preferably about 1 to about 12 carbon atoms and about 1 to about 4 heteroatoms. Preferred heteroalkenyl groups include the following groups. Preferred alkylthio groups include those groups having one or more thioether linkages and from 1 to about 12 carbon atoms, more preferably from 1 to about 8 carbon atoms, and still more preferably from 1 to about 6 carbon atoms. Alkenylthio groups having 1, 2, 3, or 4 carbon atoms are particularly preferred. Preferred alkenylsulfinyl groups include those groups having one or more sulfoxide (SO) groups and from 1 to about 12 carbon atoms, more preferably from 1 to about 8 carbon atoms, and still more preferably from 1 to about 6 carbon atoms. Alkenylsulfinyl groups having 1, 2, 3, or 4 carbon atoms are particularly preferred. Preferred alkenylsulfonyl groups include those groups having one or more sulfonyl ($SO_2$) groups and from 1 to about 12 carbon atoms, more preferably from 1 to about 8 carbon atoms, and still more preferably from 1 to about 6 carbon atoms. Alkenylsulfonyl groups having 1, 2, 3, or 4 carbon atoms are particularly preferred. Preferred aminoalkenyl groups include those groups having one or more primary, secondary and/or tertiary amine groups, and from 1 to about 12 carbon atoms, more preferably from 1 to about 8 carbon atoms, and still more preferably from 1 to about 6 carbon atoms. Aminoalkenyl groups having 1, 2, 3, or 4 carbon atoms are particularly preferred.

As used herein, "heteroalkynyl" is intended to include branched, straight-chain and cyclic saturated aliphatic hydrocarbon groups including alkynylene, having the specified number of carbon atoms and at least one heteroatom, e.g., N, O or S. Heteroalkynyl groups will typically have between about 1 and about 20 carbon atoms and about 1 to about 8 heteroatoms, preferably about 1 to about 12 carbon atoms and about 1 to about 4 heteroatoms. Preferred heteroalkynyl groups include the following groups. Preferred alkynylthio groups include those groups having one or more thioether linkages and from 1 to about 12 carbon atoms, more preferably from 1 to about 8 carbon atoms, and still more preferably from 1 to about 6 carbon atoms. Alkynylthio groups having 1, 2, 3, or 4 carbon atoms are particularly preferred. Preferred alkynylsulfinyl groups include those groups having one or more sulfoxide (SO) groups and from 1 to about 12 carbon atoms, more preferably from 1 to about 8 carbon atoms, and still more preferably from 1 to about 6 carbon atoms. Alkynylsulfinyl groups having 1, 2, 3, or 4 carbon atoms are particularly preferred. Preferred alkynylsulfonyl groups include those groups having one or more sulfonyl ($SO_2$) groups and from 1 to about 12 carbon atoms, more preferably from 1 to about 8 carbon atoms, and still more preferably from 1 to about 6 carbon atoms. Alkynylsulfonyl groups having 1, 2, 3, or 4 carbon atoms are particularly preferred. Preferred aminoalkynyl groups include those groups having one or more primary, secondary and/or tertiary amine groups, and from 1 to about 12 carbon atoms, more preferably from 1 to about 8 carbon atoms, and still more preferably from 1 to about 6 carbon atoms. Aminoalkynyl groups having 1, 2, 3, or 4 carbon atoms are particularly preferred.

As used herein, "cycloalkyl" is intended to include saturated ring groups, having the specified number of carbon atoms, such as cyclopropyl, cyclobutyl, cyclopentyl, or cyclohexyl. Cycloalkyl groups typically will have 3 to about 8 ring members.

In the term "($C_{3-6}$ cycloalkyl)$C_{1-4}$ alkyl", as defined above, the point of attachment is on the alkyl group. This term encompasses, but is not limited to, cyclopropylmethyl, cyclohexylmethyl, cyclohexylmethyl.

As used here, "alkenyl" is intended to include hydrocarbon chains of straight, cyclic or branched configuration, including alkenylene, and one or more unsaturated carbon-carbon bonds which may occur in any stable point along the chain, such as ethenyl and propenyl. Alkenyl groups typically will have 2 to about 12 carbon atoms, more typically 2 to about 12 carbon atoms.

As used herein, "alkynyl" is intended to include hydrocarbon chains of straight, cyclic or branched configuration, including alkynylene, and one or more triple carbon-carbon bonds which may occur in any stable point along the chain, such as ethynyl and propynyl. Alkynyl groups typically will have 2 to about 20 carbon atoms, more typically 2 to about 12 carbon atoms.

As used herein, "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1). Examples of haloalkyl include, but are not limited to, trifluoromethyl, trichloromethyl, pentafluoroethyl, and pentachloroethyl. Typical haloalkyl groups will have 1 to about 16 carbon atoms, more typically 1 to about 12 carbon atoms.

As used herein, "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Alkoxy groups typically have 1 to about 16 carbon atoms, more typically 1 to about 12 carbon atoms.

"Prodrugs" are intended to include any covalently bonded carriers which release the active parent drug according to formula I in vivo when such prodrug is administered to a mammalian subject. Prodrugs of a compound are prepared by modifying functional groups present in the drug compound in such a way that the modifications are cleaved, either in routine manipulation or in vivo, to the parent compound.

Combinations of substituents and/or variables are permissible only if such combinations result in stable compounds. A stable compound or stable structure is meant to imply a compound that is sufficiently robust to survive isolation to a useful degree of purity from a reaction mixture, and formulation into an effective therapeutic agent.

As used herein, the term "aliphatic" refers to a linear, branched, cyclic alkane, alkene, or alkyne. Preferred aliphatic groups in the poly(phosphoester-co-amide) polymer of the invention are linear or branched and have from 1 to 20 carbon atoms.

As used herein, the term "aryl" refers to an unsaturated cyclic carbon compound with 4n+2π electrons where n is a non-negative integer, about 5-18 aromatic ring atoms and about 1 to about 3 aromatic rings.

As used herein, the term "heterocyclic" refers to a saturated or unsaturated ring compound having one or more atoms other than carbon in the ring, for example, nitrogen, oxygen or sulfur.

All documents mentioned herein are incorporated herein in their entirety by reference.

The invention has been described in detail with reference to preferred embodiments thereof. However, it will be appreciated that those skilled in the art, upon consideration of the disclosure, may make modifications and improvements within the spirit and scope of the invention.

Synthesis

Synthetic methods of preparing compounds according to any one of Formula I-VII are not particularly limited and may include any method known to one skilled in synthetic organic chemistry.

A general synthetic procedure for preparing maleiimides is shown in scheme 1 and includes two steps. Firstly, the dibromomaleiimide intermediates were prepared by coupling substituted aniline with dibromomaleic acid in refluxing acetic acid under argon overnight. Then, the target bisthiolethanol phenyl maleiimides were obtained by following reaction with 2-mercaptoethanol in the presence of imidazole as the base in THF. For example, o-iodoaniline was coupled to 3,4-dibromomaleic acid in acetic acid refluxed overnight to form PM-01, 3,4-dibromo-1-o-iodophenyl-maleiimide in 84% yield. PM-02 was obtained in 90% yield after the reaction of PM-01 with 2-mercaptoethanol.

Scheme 1

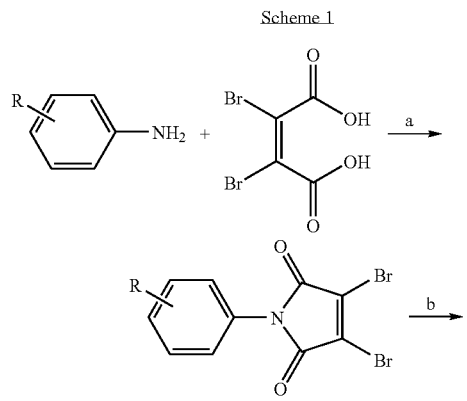

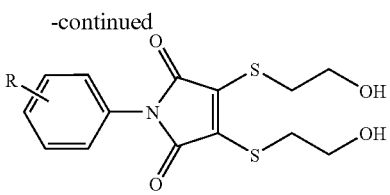

a. acetic acid, Ar, reflux, overnight; b. HSCH2CH2OH/immidazole, THF

EXAMPLE 1

General Procedure for the Preparation of 3,4-dibromomaleimides

To a stirred solution of 3,4-dibromomaleic acid in acetic acid was added phenylamine (1.1 equiv) dropwise in an ice-cooled bath. The mixture was heated to reflux overnight under argon. After cooling, the mixture was poured into ice water and extracted with ethylacetate (3×). The combined organic layers were washed with saturated sodium bicarbonate and brine and dried over magnesium sulfate. Removal of solvent gave the crude product, which was purified by flash chromatography on silica gel. The details are described below for each material.

EXAMPLE 2

N-(2-fluoro-phenyl)-3,4-dibromo-maleimide (PM-03)

See the general procedure described in Example 1. 3,4-dibromomaleic acid (100 mg, 0.36 mmol), acetic acid (5 mL) and 2-fluoro-phenylamine (42 µL, 0.4 mmol) were used to afford 100 mg (78.5%) of the title compound as a white crystal solid after purified by flash chromatography on silica gel (ethyl acetate:hexanes=1:20). m/e: 349.8 (100.0%, M+2+H+), 347.8 (51.4%, M+H+), 351.8 (48.6%, M+4+H+). $^1$H NMR (200 MHz, CDCl$_3$) δ 7.47-7.17 (m, 4H).

EXAMPLE 3

N-Biphenyl-4-yl-3,4-dibromo-maleimide (PM-19)

See the general procedure described in Example 1. 3,4-dibromomaleic acid (100 mg, 0.36 mmol), acetic acid (5 mL) and biphenyl-4-ylamine (68 mg, 0.4 mmol) were used to afford 120 mg (73.6%) of the title compound as a pale yellow crystal after purified by flash chromatography on silica gel (ethyl acetate:hexanes=1:5). m/e: 407.8 (100.0%, M+2+H+), 405.8 (51.4%, M+H+), 409.9 (48.6%, M+4+H+). $^1$H NMR (200 MHz, CDCl$_3$) δ 7.71-7.66 (m, 2H), 7.62-7.57 (m, 2H), 7.49-7.37 (m, 5H).

EXAMPLE 4

N-(4-Acetyl-phenyl)-3,4-dibromo-maleimide (PM-23)

See the general procedure described in Example 1. 3,4-dibromomaleic acid (100 mg, 0.36 mmol), acetic acid (5 mL) and biphenyl-4-ylamine (55 mg, 0.4 mmol) were used to afford 78 mg (58.1%) of the title compound as a yellow powder after purified by flash chromatography on silica gel (ethyl acetate:hexanes=1:1). m/e: 373.8 (100.0%, M+2+H+), 371.8 (51.4%, M+H$^+$), 375.8 (48.6%, M+4+H$^+$). $^1$H NMR (200 MHz, CDCl$_3$) δ 8.09-8.05 (AB, J=7 Hz, 2H), 7.56-7.49 (AB, J=7 Hz, 2H), 2.63 (s, 3H).

EXAMPLE 5

3,4-Dibromo-N-naphthalen-2-yl-maleimide (PM-33)

See the general procedure described in Example 1. 3,4-dibromomaleic acid (200 mg, 0.73 mmol), acetic acid (5 mL) and naphthalene-2-ylamine (120 mg, 0.8 mmol) were used to afford 70 mg (25%) of the title compound as a pale yellow crystal after purified by flash chromatography on silica gel (ethyl acetate:hexanes=1:10). m/e: 381.6 (100.0%, M+2+H$^+$), 379.7 (51.4%, M+H$^+$), 383.6 (48.6%, M+4+H$^+$). $^1$H NMR (200 MHz, CDCl$_3$) δ 7.96-7.84 (m, 4H), 7.57-7.52 (m, 2H), 7.45-7.40 (m, 1H).

EXAMPLE 6

General procedure for the preparation of N-phenyl-3, 4-bis-(2-hydroxy-ethylsulfanyl)-maleimides (Procedure B)

To a solution of 3,4-dibromomaleimide and imidazole (2.2 equiv) in THF was added 2-mercaptomethanol (2.2 equiv) and the mixture was stirred for 3 hours, then was added saturated ammonium chloride. The resulting solution was extracted with ethyl acetate (3×). The combined organic layers were washed with brine and dried over magnesium sulfate. Removal of solvent gave the crude product, which was purified by flash chromatography on silica gel. The details are described below for each material.

EXAMPLE 7

N-(2-fluoro-phenyl)-3,4-bis-(2-hydroxy-ethylsulfanyl)-maleimide (PM-04)

See the general procedure described in Example 6. N-(2-fluoro-phenyl)-3,4-dibromo-maleimide (80 mg, 0.23 mmol), imidazole (34.1 mg, 0.5 mmol) and 2-mercaptomethanol (35.4 μL, 0.5 mmol) were used to afford 72 mg (91.2%) of the title compound as a pale yellow solid after purified by flash chromatography on silica gel (ethyl acetate:hexanes=1:1). m/e: 344.0 (100.0%, M+H$^+$)$^+$). $^1$H NMR (200 MHz, CDCl$_3$) δ 7.47-7.17 (m, 4H), 3.92-3.87 (t, J=5.6 Hz, 4H), 3.57-3.52 (t, J=5.6 Hz, 4H), 2.26 (br, 2H).

EXAMPLE 8

N-Biphenyl-4-yl-3,4-bis-(2-hydroxy-ethylsulfanyl)-maleimide (PM-20)

See the general procedure described in Example 6. N-Biphenyl-4-yl-3,4-dibromo-maleimide (0.77 g, 1.9 mmol), imidazole (0.28 g, 4.2 mmol) and 2-mercaptomethanol (306 μL, 4.2 mmol) were used to afford 650 mg (85.6%) of the title compound as a yellow solid after purified by flash chromatography on silica gel (ethyl acetate:hexanes=1:1). m/e: 402.0 (100%, M+H$^+$). $^1$H NMR (200 MHz, CDCl$_3$) δ 7.69-7.65 (m, 2H), 7.61-7.56 (m, 2H), 7.49-7.36 (m, 5H), 3.92-3.87 (t, J=5.6 Hz, 4H), 3.57-3.52 (t, J=5.6 Hz, 4H), 2.22 (br, 2H).

EXAMPLE 9

N-(4-Acetyl-phenyl)-3,4-bis-(2-hydroxy-ethylsulfanyl-maleimide (PM-24)

See the general procedure described in Example 6. N-(4-Acetyl-phenyl)-3,4-dibromo-maleimide (58 mg, 0.16 mmol), imidazole (23.4 mg, 0.34 mmol) and 2-mercaptomethanol (25.2 μL, 0.34 mmol) were used to afford 45 mg (78.5%) of the title compound as a yellow solid after purified by flash chromatography on silica gel (ethyl acetate:hexanes=2:3). m/e: 368.0 (100.0%, M+H$^+$). $^1$H NMR (200 MHz, CDCl$_3$) δ 8.07-8.02 (AB, J=7 Hz, 2H), 7.52-7.26 (AB, J=7 Hz, 2H), 3.92-3.87 (t, J=5.6 Hz, 4H), 3.57-3.52 (t, J=5.6 Hz, 4H), 2.63 (s, 3H). 2.26 (br, 2H).

EXAMPLE 10

3,4-Bis-(2-hydroxy-ethylsulfanyl)-1-naphthalen-2-yl-maleimide (PM-34)

See the general procedure described in Example 6. 3,4-Dibromo-N-naphthalen-2-yl-maleimide (61 mg, 0.16 mmol), imidazole (24 mg, 0.35 mmol) and 2-mercaptomethanol (25.8 μL, 0.35 mmol) were used to afford 52 mg (86.5%) of the title compound as a yellow solid after purified by flash chromatography on silica gel (ethyl acetate:hexanes=2:3). m/e: 376.0 (100.0%, M+H$^+$). $^1$H NMR (200 MHz, CDCl$_3$) δ 7.94-7.81 (m, 4H), 7.54-7.45 (m, 2H), 7.44-7.40 (m, 1H), 3.94-3.88 (t, J=5.6 Hz, 4H), 3.57-3.52 (t, J=5.6 Hz, 4H), 2.26 (br, 2H).

EXAMPLE 11

Affinity Assay Using Hep3B Cells

Hep3B or JM-1 hepatoma cells were grown in tissue culture in MEM medium supplemented with 10% fetal bovine serum. Cells were plated at a density of 1×104. Inhibitor (PM-20 or related compounds) was added to the cell culture at various concentrations. Culture medium was replaced every day with new medium containing the inhibitor. After 3 days of treatment, the cells were rinsed once with PBS and frozen at −80° C. until counting. Frozen cells were thawed and incubated with the DNA-staining dye Hoescht 33258. The cell numbers were determined by measuring the dye-bound DNA fluorescence by a fluorescent plate reader.

FIG. 1 provides cell growth data for Hep3B cells contacted with various concentrations of compounds PM-02 through PM-18 of the invention. All these compounds were found to inhibit cell growth in a dose-dependent manner. In general, derivatives of PM-I, e.g., N-(phenyl)-3,4-bis-(2-hydroxyethylsulfanyl-maleimide, having a para substituent on the phenyl ring have a lower IC$_{50}$ than PM-I (IC$_{50}$=30 μM), and para-substituted compounds tend to be more active than compounds having ortho- or meta-substituted phenyl rings. Thus, PM-14 (3,4-bisthioethanol-1-p-methoxyphenyl maleiimide) showed the lowest IC$_{50}$ of compounds PM-02 to PM-18 at 6 μM.

Figure 2:
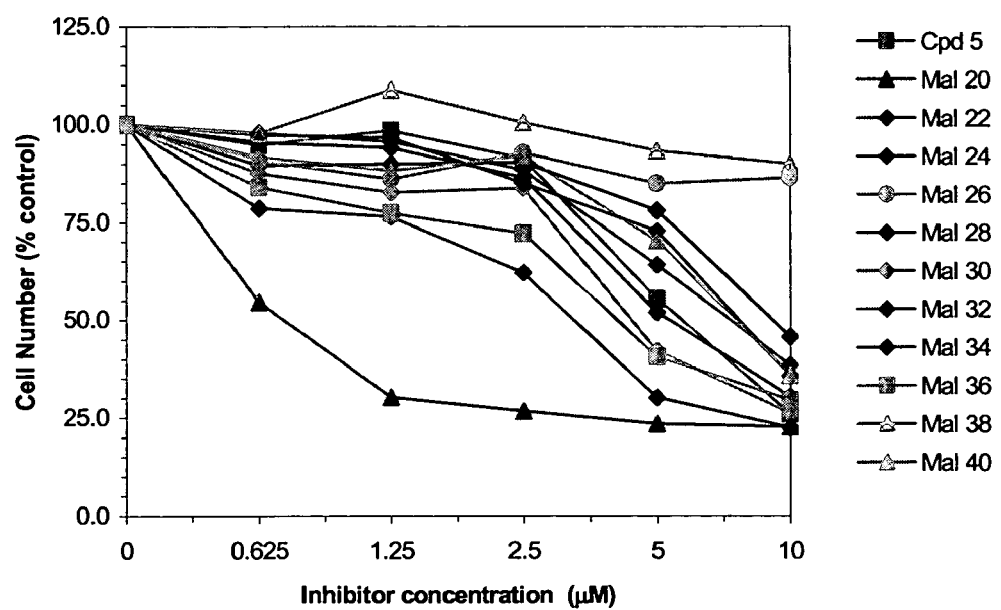
FIG. 2 is a plot of cell growth inhibition activity for 2-(2-mercaptoethanol)-3-methyl-1,4-naphthoquinone and various compounds according to Formula I.

Based on the initial structure activity relationship study, a second series of maleiimide compounds, PM-20~ PM-40, were investigated. FIG. 2 provides cell growth data for Hep3B cells contacted with various concentrations of compounds PM-20 through PM-40. Compounds PM-20 through PM-40 are active growth inhibitors of the Hep3B cell line and possess an IC$_{50}$ ranging from 700 nM to 7 μM. More particularly, PM-20, PM-34, PM-36, PM-30, and PM-28 were discovered to be more potent inhibitors than Cpd5 (2-(2-mercaptoethanol)-3-methyl-1,4-naphthoquinone) at Hep3B cell growth inhibition. PM-20 was a potent inhibitor ($IC_{50}$=700 nM) as was PM-42 ($IC_{50}$=~100 nM). Two other derivatives PM-26 and PM-38 did not inhibit Hep3B cell growth even at 10 μM.

PM-20 is a selective inhibitor of dual specificity phosphatases Cdc25A ($IC_{50}$=5 μM) and Cdc25B ($IC_{50}$=10 μM) versus Cdc25C ($IC_{50}$=40 μM) and MKP1 ($IC_{50}$=75 μM) and essentially no activity against PYP1B and CD45. It was also found that PM-20 binds to the catalytic domain of Cdc25B.

PM-20 and other compounds in the series appear to induce tyrosine phosphorylation of EGFR and ERK1/2. Inhibition of ERK1/2 phosphorylation by MEK1/2 inhibitor U0126, antagonized the growth inhibitory effect of PM-20. Cell cycle analysis revealed a block, mainly in the G1 phase of cell cycle and resulted in upregulation of tyrosine phosphorylation of cyclin dependent kinases Cdk1, 2 and 4. Our observations suggested that the mechanism of growth inhibition of these new PM analogs likely involve ERK1/2 phosphorylation and inhibition of tyrosine phosphatases that normally regulate dephosphorylation of phospho-tyrosine of Cdk1, 2 and 4. This result is not completely unexpected since the active sites of many phosphatases are very similar.

Our results show that PM-20 is a potent inhibitor of dephosphorylation of ERK 1/2 and as a consequence is a potent inhibitor of ERK signaling. We were able to show that the sustained phosphorylation of ERK is directly connected with the inhibition of tumor cell growth in vitro.

Earlier experiments designed to provide an indication of the therapeutic index of PM-20 that involved the measurement of growth inhibition of untransformed liver cells by the compound suggested that the index may be around 20. That is, the concentration of the PM-20 needed to affect normal cells is 20 times higher than that needed for tumor cells. This earlier work was confirmed.

PM-20 inhibited DNA synthesis of primary cultures of normal hepatocytes at a 10-fold higher concentration that that needed to inhibit the DNA synthesis of the Hep3B hepatoma cells.

PM-20 is at least 20-fold less toxic to normal hepatocytes than to Hep3B hepatoma cells. In vivo activity was demonstrated in an orthotopic rat tumor model. JM-1 rat hepatoma cells were seeded into livers of F344 rats. The rats were treated with intraperitoneal injections of DMSO (controls) or with 1 mg/kg of PM-20, given every other day for a total of 5 injections. The control rats had on the average 11 tumors per liver, whereas the PM-20-treated rats had 2 tumors per rat. Thus, PM-20 has considerable in vivo activity.

EXAMPLE 12

Tumor Cell Line Data

Tumor cell lines established from several human tumors (MCF7 and SKBR3, mammary carcinoma; FemX, melanoma; HR, gastric carcinoma; PCI, squamous cell carcinoma from tongue; LS180, colon carcinoma; and Hep3B, hepatocellular carcinoma) were cultured with PM-20 or PM-26 for 3 days. IC50 was determined from the growth inhibition curves. The maximum concentration of PM used in this experiment was 20 μmol/L. See also, Kar, s., et al., "PM-20, a novel inhibitor of Cdc25A, induces extracellular signal-regulated kinase ½ phosphorylation and inhibits hepatocellular carcinoma growth in vitro and in vivo", Mol. Cancer Ther. 5(6), (2006), incorporated by reference herein in its entirety.

| Organ | Cell Line | IC50 (μmol/L) PM-20 | IC50 (μmol/L) PM-26 |
|---|---|---|---|
| Breast | MCF7 | 4 | >20 |
| Breast | SKBR3 | 6 | >20 |
| Skin | FemX | 2.5 | >20 |
| Stomach | HR | 6 | >20 |
| Tongue | PCI | 2.5 | >20 |
| Colon | LS180 | 20 | >20 |
| Liver | Hep3B | 0.7 | >20 |

REFERENCES

1. Wera, S. and B. A. Hemmings, *Serine/threonine protein phosphatases. Biochem J,* 1995. 311 (Pt 1): p. 17-29.
2. Keyse, S. M., *An emerging family of dual specificity MAP kinase phosphatases. Biochim Biophys Acta,* 1995. 1265 (2-3): p. 152-60.
3. Denu, J. M., et al., *Visualization of intermediate and transition-state structures in protein-tyrosine phosphatase catalysis. Proc Natl Acad Sci USA,* 1996. 93(6): p. 2493-8.
4. Galaktionov, K., X. Chen, and D. Beach, *Cdc25 cell-cycle phosphatase as a target of c-myc. Nature,* 1996. 382(6591): p. 511-7.
5. Maehama, T. and J. E. Dixon, *The tumor suppressor, PTEN/MMAC1, dephosphorylates the lipid second messenger, phosphatidylinositol 3,4,5-trisphosphate. J Biol Chem,* 1998. 273(22): p. 13375-8.
6. Nilsson, I. and I. Hoffmann, *Cell cycle regulation by the Cdc25 phosphatase family. Prog Cell Cycle Res,* 2000. 4: p. 107-14.
7. Xia, K., et al., *Tyrosine phosphorylation of the proto-oncoprotein Raf-1 is regulated by Raf-1 itself and the phosphatase Cdc25A. Mol Cell Biol,* 1999. 19(7): p. 4819-24.
8. Sadhu, K., et al., *Human homolog of fission yeast cdc25 mitotic inducer is predominantly expressed in G2. Proc Natl Acad Sci USA,* 1990. 87(13): p. 5139-43.
9. Millar, J. B., et al., *p55CDC25 is a nuclear protein required for the initiation of mitosis in human cells. Proc Natl Acad Sci USA,* 1991. 88(23): p. 10500-4.
10. Nagata, A., et al., *An additional homolog of the fission yeast cdc25+ gene occurs in humans and is highly expressed in some cancer cells. New Biol,* 1991. 3(10): p. 959-68.
11. Jinno, S., et al., *Cdc25A is a novel phosphatase functioning early in the cell cycle. Embo J,* 1994. 13(7): p. 1549-56.
12. Molinari, M., et al., *Human Cdc25 A inactivation in response to S phase inhibition and its role in preventing premature mitosis. EMBO Rep,* 2000. 1(1): p. 71-9.
13. Lammers, R., et al., *Differential activities of protein tyrosine phosphatases in intact cells. J Biol Chem,* 1993. 268(30): p. 22456-62.
14. Galaktionov, K., et al., *CDC25 phosphatases as potential human oncogenes. Science,* 1995. 269(5230): p. 1575-7.
15. Gasparotto, D., et al., *Overexpression of CDC25A and CDC25B in head and neck cancers. Cancer Res,* 1997. 57(12): p. 2366-8.
16. Hernandez, S., et al., *cdc25 cell cycle-activating phosphatases and c-myc expression in human non-Hodgkin's lymphomas. Cancer Res,* 1998. 58(8): p. 1762-7.
17. Wu, W., et al., *Overexpression of cdc25A and cdc25B is frequent in primary non-small cell lung cancer but is not associated with overexpression of c-myc. Cancer Res,* 1998. 58(18): p. 4082-5.

18. Imoto, M., et al., *Dephostatin, a novel protein tyrosine phosphatase inhibitor produced by Streptomyces. I. Taxonomy, isolation, and characterization. J Antibiot (Tokyo)*, 1993. 46(9): p. 1342-6.
19. Cebula, R. E. B., J. L.; Boisclair, M. D.; Mansuri, M. M.; Pal, K.; Bockovich, N. J., *Synthesis and phosphatase inhibitory activity of analogs of sulfurcin. Bioorg. Med. Chem. Lett*, 1997. 7: p. 2015-2020.
20. Horiguchi, T., et al., *Dnacin A1 and dnacin B1 are antitumor antibiotics that inhibit cdc25B phosphatase activity. Biochem Pharmacol*, 1994. 48(11): p. 2139-41.
21. Borgne, A. and L. Meijer, *Sequential dephosphorylation of p34(cdc2) on Thr-14 and Tyr-15 at the prophase/metaphase transition. J Biol Chem*, 1996. 271(44): p. 27847-54.
22. Tamura, K, et al., *Cdc25 inhibition and cell cycle arrest by a synthetic thioalkyl vitamin K analogue. Cancer Res*, 2000. 60(5): p. 1317-25.
23. Ham, S. W., et al., *Naphthoquinone analogs as inactivators of cdc25 phosphatase. Bioorg Med Chem Lett*, 1998. 8(18): p. 2507-10.
24. Peng, H., et al., *Novel CDC25A phosphatase inhibitors from pyrolysis of 3-alpha-azido-B-homo-6-oxa-4-cholesten-7-one on silica gel. J Med Chem*, 1998. 41(24): p. 4677-80.
25. Koufaki, M., et al., *Alkyl and alkoxyethyl antineoplastic phospholipids. J Med Chem*, 1996. 39(13): p. 2609-14.
26. Loukaci, A. S., Isabelle Le; Samadi, Mohammad; Leclerc, Sophie; Damiens, Eve; Laurent, Meijer; Debitus, Cecile; Guyot, Michele, *Coscinosulfate, a CDC25 Phosphotase Inhibitor from the Sponge Coscinoderma Mathewsi. Bioorg. Med. Chem. Lett*, 2001. 9: p. 3049-3054.
27. Chlebowski, R. T., et al., *Vitamin K3 inhibition of malignant murine cell growth and human tumor colony formation. Cancer Treat Rep*, 1985. 69(5): p. 527-32.
28. Thor, H., et al., *The metabolism of menadione (2-methyl-1,4-naphthoquinone) by isolated hepatocytes. A study of the implications of oxidative stress in intact cells. J Biol Chem*, 1982. 257(20): p. 12419-25.
29. Nutter, L. M., et al., *Menadione: spectrum of anticancer activity and effects on nucleotide metabolism in human neoplastic cell lines. Biochem Pharmacol*, 1991. 41(9): p. 1283-92.
30. Nutter, L. M., et al., *DNA strand scission and free radical production in menadione-treated cells. Correlation with cytotoxicity and role of NADPH quinone acceptor oxidoreductase. J Biol Chem*, 1992. 267(4): p. 2474-9.

The foregoing description of the invention is merely illustrative thereof, and it is understood that variations and modifications can be effected without departing from the spirit or scope of the invention as set forth in the following claims.

What is claimed is:

1. A compound of the following Formula II:

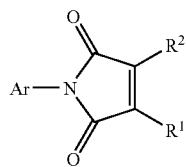

II wherein:
R$^1$ is selected from hydrogen, amino, thiol, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, or optionally substituted aminoalkyl;

R$^2$ is —X—(CH$_2$)n-Y;

Ar is phenyl or naphthyl, each of which is substituted with between 0 and 5 substituents independently selected from halogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, and optionally substituted aminoalkyl; and with the proviso that if Ar is substituted phenyl than Ar is not para-carboxy substituted phenyl;

X is O, S(O)$_p$, NH, or N(C$_{1-6}$alkyl);

Y is hydroxy, carboxylate, sulfonate, carboxamide, or amino;

n is an integer of from 1 to about 8; and p is 0, 1, or 2, or a pharmaceutically acceptable salt thereof.

2. The compound of claim 1, having the Formula III:

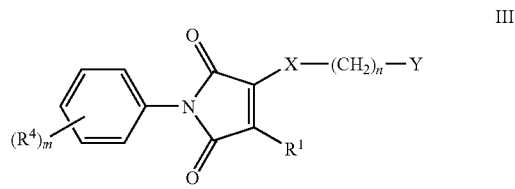

III wherein:
R$^1$ is independently selected from hydrogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, or optionally substituted aminoalkyl;

R$^4$ is selected from the group consisting of halogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, and optionally substituted aminoalkyl;

X is O, S(O)$_p$, NH, or N(C$_{1-6}$alkyl)

Y is hydroxy, carboxylate, sulfonate, carboxamide, or amino;

m is an integer of from 0 to 5;

n is an integer of from 1 to about 8; and p is 0, 1, or 2, or a pharmaceutically acceptable salt thereof.

3. The compound of claim 2, wherein
$R^1$ is selected from hydrogen, amino, thiol, hydroxy, cyano, or
$R^1$ is selected from $C_{1-6}$alkyl, $C_{2-6}$alkenyl, $C_{2-6}$alkynyl, $C_{1-6}$alkoxy, $C_{1-6}$mercaptoalkyl, mono- or di-($C_{1-6}$alkyl) amino, or $C_{1-6}$aminoalkyl, each of which is substituted with 0-2 substituents selected from halogen, hydroxy, amino, $C_{1-4}$alkoxy, cyano, carboxylate, or sulfonate;
$R^4$ is selected from the group consisting of halogen, amino, hydroxy, cyano, nitro, or
$R^4$ is selected from $C_{1-6}$alkyl, $C_{2-6}$alkenyl, $C_{2-6}$alkynyl, phenyl, naphthyl, 5 to 7 membered heteroaryl, $C_{1-6}$alkoxy, $C_{1-6}$mercaptoalkyl, mono- or di-($C_{1-6}$alkyl) amino, and $C_{1-6}$aminoalkyl, each of which is substituted with 0-4 substituents independently selected from the group consisting of halogen, hydroxy, amino, $C_{1-6}$alkyl, $C_{1-6}$alkoxy, $C_{1-6}$haloalkyl, and $C_{1-6}$haloalkoxy;
or a pharmaceutically acceptable salt thereof.

4. A compound according to Formula I:

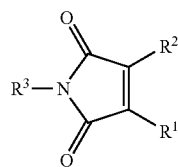

I wherein:
$R^1$ and $R^2$ are independently selected from hydrogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, or optionally substituted aminoalkyl;
$R^3$ is optionally substituted phenyl, optionally substituted biphenyl, or optionally substituted 1- or 2-naphthyl; and with the proviso that if $R^3$ is substituted phenyl than $R^3$ is not para-carboxy substituted phenyl; and
wherein at least one of $R^1$ and $R^2$ is a $C_{1-6}$mercaptoalkanol.

5. The compound of claim 4, wherein $R^3$ is biphenyl or naphthyl each of which is unsubstituted or substituted with between one and three substituents selected from the group consisting of amino, halogen, hydroxy, cyano, nitro, carboxylate, carboxamide, $C_{1-6}$alkyl, $C_{2-6}$alkenyl, $C_{2-6}$alkynyl, $C_{6-12}$aryl, $C_{3-10}$heteroaryl, $C_{1-6}$alkoxy, $C_{1-6}$mercaptoalkyl, $C_{1-6}$mercaptoalkanol, mono- or di-$C_{1-6}$alkyl amino, $C_{3-8}$cycloalkyl, $C_{2-7}$heteroalicyclic, or $C_{1-6}$aminoalkyl.

6. The compound of claim 4, wherein $R^1$ and $R^2$ are independently selected from the group consisting of $C_{1-6}$alkyl, $C_{1-6}$alkoxy, mono- and di-$C_{1-6}$alkylamino, $C_{1-6}$mercaptoalkyl, $C_{1-6}$mercaptoalkanol, $C_{2-6}$alkenyl, and $C_{2-6}$alkynyl, each of which may be optionally substituted with one or more groups selected from halogen, hydroxy, amino, carboxylate, sulfonate, cyano, and carboxamide.

7. The compound of claim 4, wherein $R^1$ is mercaptoethanol and $R^2$ is selected from the group consisting of $C_{1-6}$alkyl, $C_{1-6}$alkoxy, mono- and di-$C_{1-6}$alkylamino, $C_{1-6}$mercaptoalkyl, $C_{1-6}$mercaptoalkanol, $C_{2-6}$alkenyl, and $C_{2-6}$alkynyl, each of which may be optionally substituted with one or more groups selected from halogen, hydroxy, amino, carboxylate, sulfonate, cyano, and carboxamide; or
$R^1$ is X—$(CH_2)_n$—Y and $R^2$ is X—$(CH_2)_n$—Z, wherein X is a single bond, oxygen, sulfur or —NH—, Y is an amino group, and Z is a carboxylate or sulfonate residue.

8. The compound of claim 4, wherein
$R^1$ is mercaptoethanol and $R^2$ is selected from the group consisting of $C_{1-6}$alkyl, $C_{1-6}$alkoxy, mono- and di-$C_{1-6}$alkylamino, $C_{1-6}$mercaptoalkyl, $C_{1-6}$mercaptoalkanol, $C_{2-6}$alkenyl, and $C_{2-6}$alkynyl, each of which may be optionally substituted with one or more groups selected from halogen, hydroxy, amino, carboxylate, sulfonate, cyano, and carboxamide; or
$R^1$ is X—$(CH_2)_n$—Y and $R^2$ is X—$(CH_2)_n$—Z, wherein X is a single bond, oxygen, sulfur or —NH—, Y is an amino group, and Z is a carboxylate or sulfonate residue; and
$R^3$ is phenyl or naphthyl each of which is unsubstituted or substituted with between one and three substituents selected from the group consisting of amino, halogen, hydroxy, cyano, nitro, carboxylate, carboxamide, $C_{1-6}$alkyl, $C_{2-6}$alkenyl, $C_{2-6}$alkynyl, $C_{6-10}$carbocyclic aryl, $C_{4-10}$heteroaryl, $C_{1-6}$alkoxy, $C_{1-6}$mercaptoalkyl, mono- or di-$C_{1-6}$alkyl amino, $C_{3-8}$cycloalkyl, $C_{2-7}$heteroalicyclic, or $C_{1-6}$aminoalkyl.

9. The compound of claim 2, wherein,
$R^1$ is —X—$(CH_2)_n$—Y, or —X—$(CH_2)_n$—Z, wherein
each X is independently $S(O)_p$;
each Y is independently an amino group,
each Z is independently a carboxylate or sulfonate group;
each n is independently 1-4; and
each p is independently 0, 1, or 2,
or a pharmaceutically acceptable salt thereof.

10. The compound of claim 2, wherein n is a number from 1 to 3; and
$R^4$ is selected from the group consisting of halogen, amino, hydroxy, cyano, nitro, $C_{1-6}$alkyl, $C_{2-6}$alkenyl, $C_{2-6}$alkynyl, phenyl, tolyl, $C_{1-6}$alkoxy, $C_{1-6}$mercaptoalkyl, mono- or di-$C_{1-6}$alkyl amino, $C_{3-8}$cycloalkyl, $C_{2-7}$heteroalicyclic, and $C_{1-6}$aminoalkyl, or a pharmaceutically acceptable salt thereof.

11. The compound of claim 2, wherein
X is independently sulfur;
n is independently 2;
Y is independently hydroxyl;
$R^1$ is independently 2-hydroxyethanthiol;
$R^4$ is independently selected from the group consisting of phenyl, tolyl, $C_{1-4}$alkyl, $C_{1-4}$alkoxy, halogen, halo$C_{1-4}$alkyl, and halo$C_{1-4}$alkoxy, or a pharmaceutically acceptable salt thereof.

12. A compound of claim 1 having the following Formula V:

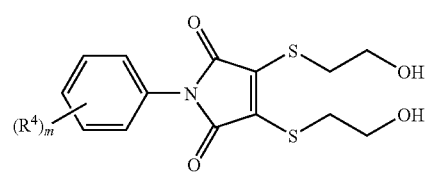

V wherein
each $R^4$ is independently selected from the group consisting of halogen, amino, hydroxy, cyano, nitro, or each $R^4$ is independently selected from $C_{1-6}$alkyl, $C_{2-6}$alkenyl, $C_{2-6}$alkynyl, phenyl, naphthyl, 5 to 7 membered heteroaryl, $C_{1-6}$alkoxy, $C_{1-6}$mercaptoalkyl, mono- or di-($C_{1-6}$alkyl)amino, and $C_{1-6}$aminoalkyl, each of which is substituted with 0-4 substituents independently selected from the group consisting of halogen, hydroxy, amino, $C_{,1-6}$alkyl, $C_{,1-6}$alkoxy, $C_{1-6}$haloalkyl, and $C_{1-6}$haloalkoxy; and m is an integer that is 0 to 4.

13. A compound of claim 12, wherein m is a number from 1 to 3; and
$R^4$ is selected from the group consisting of halogen, amino, hydroxy, cyano, nitro, $C_{1-6}$alkyl, $C_{2-6}$alkenyl, $C_{2-6}$alkynyl, phenyl, tolyl, $C_{1-6}$alkoxy, $C_{1-6}$mercaptoalkyl, mono- or di-$C_{1-6}$alkyl amino, $C_{3-8}$cycloalkyl, $C_{2-7}$heteroalicyclic, and $C_{1-6}$aminoalkyl.

14. A compound of claim 1 having the following Formula VI:

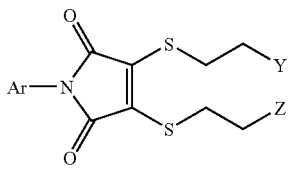

wherein Ar is phenyl or naphthyl each of which is unsubstituted or substituted with between one and three substituents selected from the group consisting of amino, halogen, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, or optionally substituted aminoalkyl;

Y is amino or mono- or di-($C_{1-4}$alkyl)amino; and

Z is a carboxylate or sulfonate group, or a pharmaceutically acceptable salt thereof.

15. A compound of claim 1 having the following Formula VII:

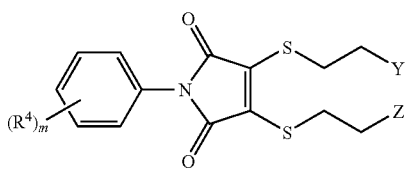

wherein
each $R^4$ is independently selected from the group consisting of halogen, amino, hydroxy, cyano, nitro, or
each $R^4$ is independently selected from $C_{1-6}$alkyl, $C_{2-6}$alkenyl, $C_{2-6}$alkynyl, phenyl, naphthyl, 5 to 7 membered heteroaryl, $C_{1-6}$alkoxy, $C_{1-6}$mercaptoalkyl, mono- or di-($C_{1-6}$alkyl)amino, and $C_{1-6}$aminoalkyl, each of which is substituted with 0-4 substituents independently selected from the group consisting of halogen, hydroxy, amino, $C_{1-6}$alkyl, $C_{1-6}$alkoxy, $C_{1-6}$haloalkyl, and $C_{1-6}$haloalkoxy;

m is an integer that is 0 to 4;

Y is amino or mono- or di-($C_{1-4}$alkyl)amino; and

Z is a carboxylate or sulfonate group, or a pharmaceutically acceptable salt thereof.

16. A compound according to Formula III:

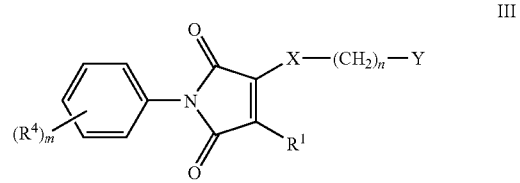

wherein:
R is selected from hydrogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, or optionally substituted aminoalkyl;

each $R^4$ is independently selected from the group consisting of halogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, and optionally substituted aminoalkyl, and with the proviso that $R^4$ is not a para-carboxy substituent;

X is O, S, NH, or N($C_{1-6}$alkyl);

Y is hydroxy, carboxylate, sulfonate, amino;

m is an integer of from 0 to 5;

each n is independently an integer of from 1 to about 8; and pharmaceutically acceptable salts thereof.

17. The compound of claim 16, wherein $R^4$ is selected from the group consisting of halogen, amino, hydroxy, cyano, nitro, carboxylate, carboxamide, $C_{1-6}$alkyl, $C_{2-6}$alkenyl, $C_{2-6}$alkynyl, phenyl, tolyl, $C_{1-6}$alkoxy, $C_{1-6}$mercaptoalkyl, mono- or di-$C_{1-6}$alkyl amino, $C_{3-8}$cycloalkyl, $C_{2-7}$heteroalicyclic, and $C_{1-6}$aminoalkyl.

18. The compound of claim 16, wherein X is S, and Y is OH.

19. The compound of claim 16, wherein X—$(CH_2)_n$—Y, taken in combination is a mercaptoethanol group.

20. The compound of claim 16, wherein $R^1$ is selected from the group consisting of $C_{1-6}$alkyl, $C_{1-6}$alkoxy, mono- and di-$C_{1-6}$alkylamino, $C_{1-6}$mercaptoalkyl, $C_{2-6}$alkenyl, and $C_{2-6}$alkynyl, each of which may be optionally substituted with one or more groups selected from halogen, hydroxy, amino, carboxylate, sulfonate, cyano, and carboxamide.

21. The compound of claim 16, wherein m is 1 and $R^4$ is halogen, amino, hydroxy, cyano, nitro, carboxylate, carboxamide, $C_{1-6}$alkyl, $C_{2-6}$alkenyl, $C_{2-6}$alkynyl, phenyl, tolyl, 5- or 6-member heterocycles having between 1 and 3 ring heteroatoms selected from N, O, and S, $C_{1-6}$alkoxy, $C_{1-6}$mercaptoalkyl, $C_{1-6}$mercaptoalkanol, mono- or di-$C_{1-6}$alkyl amino, $C_{3-8}$cycloalkyl, or $C_{1-6}$aminoalkyl.

22. A compound according to Formula IV:

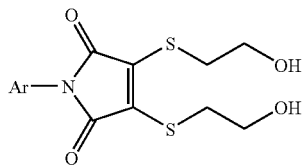

wherein:
  Ar is phenyl or naphthyl each of which is unsubstituted or substituted with between one and three substituents selected from the group consisting of amino, halogen, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, or optionally substituted aminoalkyl and with the proviso that if Ar is substituted phenyl than Ar is not para-carboxy substituted phenyl.

23. The compound of claim 22, wherein Ar is phenyl or naphthyl each of which is unsubstituted or substituted with between one and five groups selected from the group consisting of halogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, or optionally substituted aminoalkyl.

24. The compound of claim 22, wherein Ar is phenyl or naphthyl each of which is unsubstituted or substituted with a group selected from the group consisting of halogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mercaptoalkyl, optionally substituted mono- or di-alkyl amino, optionally substituted cycloalkyl, optionally substituted heteroalicyclic, or optionally substituted aminoalkyl.

25. The compound of claim 22, wherein Ar is phenyl or naphthyl each of which is unsubstituted or substituted with between one and three substituents selected from the group consisting of amino, halogen, hydroxy, cyano, nitro, carboxylate, carboxamide, $C_{1-6}$alkyl, $C_{2-6}$alkenyl, $C_{2-6}$alkynyl, phenyl, tolyl, 5- or 6-member heterocycles having between 1 and 3 ring heteroatoms selected from N, O, and S, $C_{1-6}$alkoxy, $C_{1-6}$mercaptoalkyl, $C_{1-6}$mercaptoalkanol, mono- or di-$C_{1-6}$ alkyl amino, $C_{3-8}$cycloalkyl, or $C_{1-6}$aminoalkyl.

26. A pharmaceutical composition comprising one or more compounds according to claim 1 and a pharmaceutically acceptable carrier.

27. A method of treating wherein the cancer is liver cancer, breast cancer, skin cancer, stomach cancer, tongue cancer, or colon cancer after cancer. comprising administering a compound or pharmaceutical composition having a compound of claim 1 to a patient suffering from cancer.

28. The method of claim 27, wherein the cancer comprises cells which over-express at least one phosphatase protein.

29. The method of claim 27, wherein the compound is capable of inhibiting at least one phosphatase protein.

30. The method of claim 27, wherein the compound is capable of inhibiting at least one dual specificity phosphatase protein.

31. The method of claim 30, wherein the compound is capable of inhibiting at least one Cdc25 protein.

32. The method of claim 27, wherein the patient is a mammal.

33. The method of claim 27, wherein the patient is a primate or human.

34. A method of inhibiting a dual specificity phosphatase activity comprising contacting a compound or pharmaceutical composition having a compound of claim 1 such that the enzymatic activity of the dual specificity phosphatase protein is reduced.

35. The method of claim 34, wherein inhibition of dual specificity phosphatase activity is done in vitro.

36. The method of claim 34, wherein the inhibition of dual specificity phosphatase activity is done in vivo.

37. The method of claim 34, wherein the dual specificity phosphatase is a Cdc25 protein.

38. The method of claim 37, wherein the Cdc25 protein is selected from the group consisting of Cdc25A, Cdc25B, Cdc25C, or a combination thereof.

39. The method of claim 34, wherein the inhibition of dual specificity phosphatase activity is done in a mammal.

40. A compound selected from the group consisting of 3,4-Bis-(2-hydroxy-ethylsulfanyl)-1-phenyl-pyrrole-2,5-dione;
  3,4-Bis-(2-hydroxy-ethylsulfanyl)-1-(2-iodophenyl)-pyrrole-2,5-dione;
  3,4-Bis-(2-hydroxy-ethylsulfanyl)-1-(2-fluorophenyl)-pyrrole-2,5-dione;
  3,4-Bis-(2-hydroxy-ethylsulfanyl)-1-(4-fluorophenyl)-pyrrole-2,5-dione;
  3,4-Bis-(2-hydroxy-ethylsulfanyl)-1-(4-chlorophenyl)-pyrrole-2,5-dione;
  3,4-Bis-(2-hydroxy-ethylsulfanyl)-1-(3-methoxyphenyl)-pyrrole-2,5-dione;
  3,4-Bis-(2-hydroxy-ethylsulfanyl)-1-(4-methoxyphenyl)-pyrrole-2,5-dione;
  3,4-Bis-(2-hydroxy-ethylsulfanyl)-1-(meta-tolyl)-pyrrole-2,5-dione;
  3,4-Bis-(2-hydroxy-ethylsulfanyl)-1-(4-chloro-2-methylphenyl) -pyrrole-2,5-dione;
  1-Biphenyl-4-yl-3,4-bis-(2-hydroxy-ethylsulfanyl)-pyrrole-2,5-dione;
  4-[3,4-Bis-(2-hydroxy-ethylsulfanyl)-2,5-dioxo-2,5-dihydro-pyrrol-1-yl]-benzonitrile;
  1-(4-Acetyl-phenyl)-3,4-bis-(2-hydroxy-ethylsulfanyl)-pyrrole-2,5-dione;
  N-{4-[3,4-Bis-(2-hydroxy-ethylsulfanyl)-2,5-dioxo-2,5-dihydro-pyrrol-1-yl]-phenyl}-acetamide;
  3,4-Bis-(2-hydroxy-ethylsulfanyl)-1-(4-ethoxyphenyl)-pyrrole-2,5-dione;
  3,4-Bis-(2-hydroxy-ethylsulfanyl)-1-(4-propoxyphenyl)-pyrrole-2,5-dione;
  3,4-Bis-(2-hydroxy-ethylsulfanyl)-1-(3,5-dimethoxyphenyl)-pyrrole-2,5-dione;
  3,4-Bis-(2-hydroxy-ethylsulfanyl)-1-naphthalen-2-yl-pyrrole-2,5-dione;

3,4-Bis-(2-hydroxy-ethylsulfanyl)-1-(trifluoromethoxyphenyl)-pyrrole-2,5-dione;

1-(4-Benzyloxy-phenyl)-3,4-bis-(2-hydroxy-ethylsulfanyl)-pyrrole-2,5-dione;

1-(4-Dimethylamino-phenyl)-3,4-bis-(2-hydroxy-ethylsulfanyl)-pyrrole-2,5-dione; and 1-(4'-nitro-biphenyl-4-yl)-3,4-bis-(2-hydroxy-ethylsulfanyl)-pyrrole-2,5-dione; or a pharmaceutically acceptable salts thereof.

41. The method of claim 27, wherein the cancer is liver cancer, breast cancer, skin cancer, stomach cancer, tongue cancer, or colon cancer.

* * * * *